United States Patent
Murakami et al.

(10) Patent No.: US 10,335,550 B2
(45) Date of Patent: Jul. 2, 2019

(54) PHARMACEUTICAL INJECTION DEVICE

(71) Applicant: PHC Holdings Corporation, Minato-ku, Tokyo (JP)

(72) Inventors: Kenji Murakami, Ehime (JP); Masato Kagiyama, Ehime (JP); Takeshi Imada, Ehime (JP); Tooru Aoki, Ehime (JP)

(73) Assignee: PHC HOLDINGS CORPORATION, Tokyo (JP)

( * ) Notice: Subject to any disclaimer, the term of this patent is extended or adjusted under 35 U.S.C. 154(b) by 270 days.

(21) Appl. No.: 15/306,110

(22) PCT Filed: Mar. 3, 2015

(86) PCT No.: PCT/JP2015/056160
§ 371 (c)(1),
(2) Date: Oct. 24, 2016

(87) PCT Pub. No.: WO2015/163009
PCT Pub. Date: Oct. 29, 2015

(65) Prior Publication Data
US 2017/0043092 A1 Feb. 16, 2017

(30) Foreign Application Priority Data

Apr. 25, 2014 (JP) .................. 2014-091446
Apr. 25, 2014 (JP) .................. 2014-091529

(51) Int. Cl.
*A61M 5/20* (2006.01)
*A61M 5/24* (2006.01)

(52) U.S. Cl.
CPC ............ *A61M 5/2422* (2013.01); *A61M 5/20* (2013.01); *A61M 5/24* (2013.01);
(Continued)

(58) Field of Classification Search
CPC ........................................... A61M 2005/2414
See application file for complete search history.

(56) References Cited

U.S. PATENT DOCUMENTS

| | | |
|---|---|---|
| 5,228,883 A | 7/1993 | Blakely et al. |
| 5,599,316 A | 2/1997 | Blakely |

(Continued)

FOREIGN PATENT DOCUMENTS

| | | |
|---|---|---|
| JP | H5-146475 A | 6/1993 |
| JP | H08-201899 A | 8/1996 |

(Continued)

OTHER PUBLICATIONS

The Office Action from the corresponding Japanese Patent Application No. 2016-514763 dated Aug. 29, 2017.

(Continued)

*Primary Examiner* — Bhisma Mehta
*Assistant Examiner* — Matthew A Engel
(74) *Attorney, Agent, or Firm* — Wenderoth, Lind & Ponack, L.L.P.

(57) ABSTRACT

A pharmaceutical injection device includes a main body case, a cartridge holder, a latching receiver, a driver, and a manipulation component. The cartridge holder has a holding space and a holder latching component. The holding space is capable of holding a pharmaceutical cartridge. The latching receiver is configured to latch or release the holder latching component according to whether the cartridge holder is closed or open. The driver is configured to automatically release a latching of the latching receiver and the holder latching component. The manipulation component is configured to manually release the latching of the latching receiver and the holder latching component by moving the latching receiver upon being subjected to external pressure. The driver or the manipulation component is configured to (Continued)

release the latching between the latching receiver and the holder latching component.

8 Claims, 14 Drawing Sheets

(52) U.S. Cl.
CPC . *A61M 2005/2414* (2013.01); *A61M 2205/10* (2013.01); *A61M 2205/50* (2013.01); *A61M 2205/52* (2013.01); *A61M 2205/581* (2013.01); *A61M 2205/583* (2013.01)

(56) References Cited

U.S. PATENT DOCUMENTS

| | | | |
|---|---|---|---|
| 5,903,791 A | 5/1999 | Okada | |
| 7,967,784 B2 | 6/2011 | Pongpairochana et al. | |
| 8,512,285 B2 | 8/2013 | Bruggemann et al. | |
| 2007/0197968 A1* | 8/2007 | Pongpairochana | A61M 5/20 604/131 |
| 2012/0116311 A1 | 5/2012 | Bruggemann et al. | |
| 2012/0271233 A1* | 10/2012 | Bruggemann | A61M 5/14546 604/131 |
| 2014/0114258 A1 | 4/2014 | Day | |
| 2015/0165121 A1* | 6/2015 | Murakami | A61M 5/20 604/154 |
| 2016/0015910 A1* | 1/2016 | Mukai | A61M 5/20 206/365 |

FOREIGN PATENT DOCUMENTS

| | | |
|---|---|---|
| JP | 2003-228119 A | 8/2003 |
| JP | 4614621 B | 10/2010 |
| JP | 2012-050847 A | 3/2012 |
| JP | 2012-513786 A | 6/2012 |
| JP | 2013-505037 A | 2/2013 |
| JP | 2014-516700 A | 7/2014 |
| WO | 02/051475 A1 | 7/2002 |
| WO | 2010/076275 A1 | 7/2010 |
| WO | 2011/032961 A1 | 3/2011 |
| WO | 2012/160157 A1 | 11/2012 |
| WO | 2013/186997 A1 | 12/2013 |

OTHER PUBLICATIONS

Internationanl Search Report of corresponding PCT Application No. PCT/JP2015/056160 dated Jun. 16, 2015.

* cited by examiner

PHARMACEUTICAL INJECTION DEVICE

PRIORITY

This is a National Stage Application under 35 U.S.C. § 365 of International Application PCT/JP2015/056160, with an international filing date of Mar. 3, 2015, which claims priority to Japanese Patent Application No. 2014-091446 filed on Apr. 25, 2014 and Japanese Patent Application No. 2014-091529 filed on Apr. 25, 2014. The entire disclosures of International Application PCT/JP2015/056160, Japanese Patent Application No. 2014-091446 and Japanese Patent Application No. 2014-091529 are hereby incorporated herein by reference.

TECHNICAL FIELD

Certain implementations of the present invention relate to a pharmaceutical injection device for injecting insulin, growth hormone, or another such pharmaceutical, for example.

BACKGROUND

A pharmaceutical injection device is an injection device that holds a pharmaceutical cartridge in its interior, and that is used to inject the pharmaceutical in the pharmaceutical cartridge into a patient's body, etc.

A pharmaceutical injection device may include a main body housing, a piston, and an end stop switch. The main body housing is a member that holds the various members of the pharmaceutical injection device, and forms the exterior of the pharmaceutical injection device. The piston is inserted into a pharmaceutical cartridge to discharge the pharmaceutical inside the pharmaceutical cartridge. The end stop switch is hit by the piston after the piston has been pulled out as far as it will go from the pharmaceutical cartridge. When the piston hits the end stop switch, the end stop switch detects that the piston has been pulled out as far as it will go from the pharmaceutical cartridge. According to this detection result, the stopping device of the pharmaceutical cartridge is disengaged, allowing access for replacing the pharmaceutical cartridge.

In a pharmaceutical injection device, let us assume that a problem has occurred for some reason in the electronic controller used for electrically driving the pharmaceutical injection device. Let us then assume that the end stop switch is unable to operate. If this happens, even when hit by the piston, the end stop switch will not be able to detect that the piston has been pulled out as far as it will go from the pharmaceutical cartridge. Thus, the stopping device of the pharmaceutical cartridge will not be disengaged, and the user will be unable to remove the pharmaceutical cartridge from the pharmaceutical injection device.

SUMMARY

In view of this, it is an object of certain implementations to provide a pharmaceutical injection device with which the pharmaceutical cartridge can be removed from the pharmaceutical injection device even if the pharmaceutical injection device cannot be driven automatically by powered drive.

The pharmaceutical injection device may comprise a main body case, a cartridge holder, a latching receiver, a driver, and a manipulation component. The cartridge holder has a holding space and a holder latching component. The holding space is provided in the interior of the main body case so as to be openable and closeable with respect to the side face of the main body case, and is capable of holding a pharmaceutical cartridge. The latching receiver latches or releases the holder latching component according to whether the cartridge holder is closed or open. The driver automatically releases the latching of the latching receiver and the holder latching component by driving the latching receiver upon receiving power. The manipulation component manually releases the latching of the latching receiver and the holder latching component by moving the latching receiver upon being subjected to external pressure. The driver or the manipulation component releases latching between the latching receiver and the holder latching component.

The cartridge holder here is used to hold a pharmaceutical cartridge. When the cartridge holder is closed with respect to the main body case, the holder latching component of the cartridge holder is latched to the latching receiver, and the pharmaceutical cartridge is held in the interior of the main body case.

With the above configuration, the driver or the manipulation component releases latching between the latching receiver and the holder latching component.

That is, when it is time to replace the pharmaceutical cartridge, the user presses a specific button, etc. Upon receiving this input, the driver receives power and automatically drives the latching receiver. This automatically unlatches the latching receiver from the holder latching component of the cartridge holder, and opens up the cartridge holder.

Alternatively, the user may operate the manipulation component manually to replace the pharmaceutical cartridge. With manual operation of the manipulation component, the latching receiver is moved without any power being supplied. Then, the latching receiver is unlatched from the holder latching component of the cartridge holder to open up the cartridge holder.

Thus, the cartridge holder is put into its open state by either the driver or the manipulation component. That is, the latching receiver either is driven automatically by the driver that has received power, or is moved without receiving power by operating the manipulation component manually. For example, there may be situations in which the latching receiver cannot be automatically driven under power because of a problem with the power supply or the like. In such a case, the user can manually move the latching receiver (without electrical power) to unlatch the latching receiver from the holder latching component. Thus, the user can open up the cartridge holder and take out the pharmaceutical cartridge.

The pharmaceutical injection device may have a holder latching component and the latching receiver are formed along the direction in which the manipulation component moves the latching receiver with external pressure.

With the above configuration, the holder latching component is latched to the latching receiver by fitting the holder latching component and the latching receiver together. The shapes of the holder latching component and the latching receiver run along the direction in which the latching receiver is moved manually under external pressure.

More specifically, the protrusion direction of the portion where the holder latching component and the latching receiver are latched together runs along the direction in which the latching receiver is moved manually. Thus, the direction in which the latching receiver separates from the holder latching component runs along the direction in which the latching receiver is moved by the external pressure. Consequently, the latching of the holder latching component and the latching receiver can be released by manually moving the latching receiver with external pressure.

The pharmaceutical injection device may have a part of the manipulation component which consists of a protrusion that sticks out farther than the other part, the latching receiver being manually moved by the application of external pressure to the protrusion, and this releases latching between the latching receiver and the holder latching component.

With the above configuration, because the manipulation component has a protrusion, the user can easily operate the manipulation component by hooking the protrusion with a finger, etc. The latching receiver can also be easily operated by means of this manual operation of the protrusion. Thus, even if a problem with the supply of power or the like should occur, and the latching receiver cannot be driven electrically, the cartridge holder can still be opened by manually moving the latching receiver (without any electrical power).

The pharmaceutical injection device may have a protrusion provided to an opening inside the main body case.

With the above configuration, the protrusion is provided to an opening inside the main body case. Accordingly, this prevents the protrusion from coming into contact with the user's hand, another member, or the like and accidentally operating the device.

The pharmaceutical injection device may have an opening which defines the movable range when the protrusion is subjected to the external pressure.

With the above configuration, the protrusion is provided to an opening inside the main body case. The protrusion is able to move within the range of this opening. The user can smoothly move the protrusion within the range of the opening, and the latching of the latching receiver and the holder latching component can be released by this movement of the protrusion.

The pharmaceutical injection device may have a power supply holding space for holding a removable power supply is provided in the interior of the main body case. Here, the opening in the main body case is provided to the power supply holding space.

With the above configuration, a power supply holding space for holding a removable power supply, such as a battery, is provided in the interior of the main body case. An opening is provided to this power supply holding space, and the protrusion of the manipulation component is located in the opening.

If there is a problem with the supply of power, etc., and the latching receiver cannot be driven electrically, the user first takes out the power supply. Then, the user operates the protrusion inside the opening in the power supply holding space, and manually moves the latching receiver. This allows the latching receiver to be unlatched from the holder latching component by moving the latching receiver manually (without any electrical power). The user can thus open up the cartridge holder.

The protrusion is provided inside the power supply holding space of the main body case, and does not stick out on the outside of the main body case. This prevents accidental operation that the protrusion come into contact with the user's hand, another member, or the like.

The pharmaceutical injection device may comprise a power supply, a piston, a piston drive force generator, a controller, a power path controller, and a switch. The piston is inserted into or pulled out of the pharmaceutical cartridge. The piston drive force generator generates drive force supplied to the piston. The controller controls the piston drive force generator upon receiving power from the power supply. The power path controller allows power from the power supply to be supplied directly to the piston drive force generator. The switch receives a command for whether or not to supply the power from the power supply directly to the piston drive force generator, and transfers the command to the power path controller.

With the above configuration, the piston drive force generator generates the drive force required for the piston either to be inserted into the pharmaceutical cartridge or to be pulled out of the pharmaceutical cartridge. When the switch has not been operated, the piston drive force generator generates piston drive force under the control of the controller that has received power from the power supply. Thus, the piston is driven by the drive force generated under the control of the controller.

On the other hand, when the switch is operated, the switch accepts the supply of power from the power supply directly to the piston drive force generator. The power path controller then supplies power from the power supply directly to the piston drive force generator on the basis of the switch operation. For example, the power path controller produces a power path for electrically connecting the power supply directly to the piston drive force generator. This operation of the switch provides power from the power supply directly to the piston drive force generator, without it being under the control of the controller.

Here, let us assume that the piston has been inserted into the pharmaceutical cartridge, and the piston drive force generator can no longer be controlled by the controller. Thus, the piston drive force generator cannot generate piston drive force under the control of the controller. Since the piston is inserted into the pharmaceutical cartridge at this point, the pharmaceutical cartridge cannot be taken out.

Even in this scenario, the user can operate the switch so that the piston drive force generator receives the supply of power directly from the power supply, allowing piston drive force to be generated. That is, even if control by the controller becomes impossible, the piston drive force generator will still be able to generate piston drive force. Therefore, the piston that has been inserted into the pharmaceutical cartridge can be pulled out of the pharmaceutical cartridge. Also, if the piston is pulled out of the pharmaceutical cartridge, the pharmaceutical cartridge can be removed without interference from the cartridge holder.

The pharmaceutical injection device may be configured such that when the switch is not operated, the power path controller connects the piston drive force generator to the power supply via the controller, and provides power from the power supply to the piston drive force generator via the controller. On the other hand, when the switch is operated, the power path controller connects the piston drive force generator to the power supply via the controller, while connecting the piston drive force generator directly to the power supply to provide the power from the power supply directly to the piston drive force generator.

With the above configuration, even when the switch has been operated, power from the power supply is still supplied to the controller, and power from the power supply is also supplied directly to the piston drive force generator. There are situations in which another driver can be controlled even though the controller cannot control the piston drive force generator. Thus, even when the switch has been operated, power can be supplied directly from the power supply to the piston drive force generator to drive the piston, while supplying power to the controller to operate a driver that can be controlled by the controller.

Furthermore, once a controller that was inoperable becomes operable, the piston drive force generator can generate piston drive force on the basis of the power from the controller.

The pharmaceutical injection device may be configured such that when the switch is not operated, the power path controller connects the piston drive force generator to the power supply via the controller, and provides power from the power supply to the piston drive force generator via the controller. On the other hand, when the switch is operated, the power path controller connects the power supply and the controller, disconnects the controller from the piston drive force generator, and connects the piston drive force generator directly to the power supply to provide the power from the power supply directly to the piston drive force generator.

With the above configuration, even if the switch is operated, power from the power supply is still supplied to the controller, and power from the power supply is also supplied directly to the piston drive force generator. There are situations in which another driver can be controlled even though the controller cannot control the piston drive force generator. Thus, even when the switch has been operated, power can be supplied directly from the power supply to the piston drive force generator to drive the piston, while operating a driver that can be controlled by the controller.

Also, when the switch has been operated, the controller is not connected to the piston drive force generator. Thus, the piston drive force generator will not be affected by accidental control from the controller even if the controller is accidentally operated.

The pharmaceutical injection device may be configured such that when the switch is operated, the power path controller provides the power from the power supply directly to the piston drive force generator.

With the above configuration, the operation of the switch is coupled with the production of a power path that electrically connects the power supply directly to the piston drive force generator. That is, the user operates the switch when power from the power supply is provided directly to the piston drive force generator.

Conversely, the user stops operating the switch when power from the power supply is provided via the controller and power from the power supply is not supplied directly to the drive force generator. Thus, whether to supply power from the power supply directly to the drive force generator or to supply power from the power supply to the drive force generator via the controller is determined by whether or not the switch is operated.

Thus, how the power is supplied to the drive force generator is obvious to the user, and this makes the device easy to operate.

The pharmaceutical injection device may have a switch is provided in a hole in the outer wall of the main body case.

With the above configuration, since the switch is provided in a hole in the outer wall of the main body case, this prevents accidental operation should the switch come into contact with the user's hand, another member, or the like.

Preferably, the pharmaceutical injection device comprises a main body case, a cartridge holder, and an injection needle mounting component. The cartridge holder has a holding space and a holder-side connector. The holding space is a space in which the pharmaceutical cartridge can be held. The holder-side connector is provided at the end of the holding space. The injection needle mounting component is substantially cylindrical, and connects an injection needle component to the cartridge holder. The injection needle mounting component has a main body part, a convex part, and a first connector. The convex part sticks out from the outer face of the main body part. The first connector is connected to the holder-side connector of the cartridge holder, and is formed continuously with the main body part.

With the above configuration, the cartridge holder is used to hold a pharmaceutical cartridge. Usually, when it is time to replace the pharmaceutical cartridge, the user presses a specific button or the like to drive a driver that opens up the cartridge holder. The user removes the used pharmaceutical cartridge from the cartridge holder, and inserts a fresh pharmaceutical cartridge into the cartridge holder.

There may be situations in which the driver has problems in opening the cartridge holder, or in which there are problems with the power supply that supplies power to the driver and the controller of the driver. In such a situation, the cartridge holder cannot be opened by the driver as discussed above, and the pharmaceutical cartridge cannot be taken out.

With the above-mentioned pharmaceutical injection device, the injection needle mounting component is fixed to the cartridge holder by connecting the first connector of the injection needle mounting component to the holder-side connector of the cartridge holder. Since only the first connector is connected to the holder-side connector at this point, the convex part sticks out from the outer surface of the cartridge holder. The user can apply pressure to the convex part by pulling, turning, etc., with a tool, a hand, etc., and thereby pull the injection needle mounting component away from the cartridge holder.

The user can thus use a tool, a hand, or the like to remove the pharmaceutical cartridge from the cartridge holder from which the injection needle mounting component has been removed. That is, even if a problem should occur in the cartridge holder driver, the controller, the power supply, etc., the pharmaceutical cartridge can still be taken out of the cartridge holder.

Preferably, the holder-side connector is provided to the end of the cartridge holder. Also, when the first connector of the injection needle mounting component is connected to the holder-side connector, the convex part sticks out from the end of the cartridge holder.

With the above pharmaceutical injection device, the injection needle mounting component is fixed to the cartridge holder by connecting the first connector of the injection needle mounting component to the holder-side connector of the cartridge holder. At this point, the convex part sticks out from the end of the cartridge holder.

Thus, if a problem should occur in the cartridge holder driver, the controller, the power supply, etc., the user can use a tool, a hand, or the like to apply pressure to the convex part sticking out from the end of the cartridge holder, and thereby pull the injection needle mounting component away from the cartridge holder. Thus, the user can take the pharmaceutical cartridge out of the cartridge holder from which the injection needle mounting component has been removed.

Preferably, the injection needle mounting component further has a second connector. The second connector is provided on the opposite side from the first connector with main body part, and, with the above configuration which an injection needle component is connected thereto, the injection needle mounting component has the second connector to which the injection needle component is connected, the convex part, and the first connector that is connected to the holder-side connector. The injection needle component can be attached to the injection needle mounting component via the second connector. This allows the injection needle component to be attached to the end of the cartridge holder via the injection needle mounting component.

Preferably, the first connector, the convex part, the main body part, and the second connector are formed integrally.

With the above configuration, since the first connector, the convex part, the main body part, and the second connector are formed integrally in the injection needle mounting component, the fit is snugger when the injection needle component is attached to the injection needle mounting component. Also, the injection needle mounting component is easier to manufacture than when first connector, the convex part, the main body part, and the second connector are formed separately.

Preferably, the convex part is formed more to the first connector side than the second connector side in the main body part.

With the above configuration, the injection needle mounting component is fixed to the cartridge holder by connecting the first connector of the injection needle mounting component to the holder-side connector of the cartridge holder. If a problem with the driver, etc., should make it impossible to open the cartridge holder, the user applies pressure to the convex part with a tool, a hand, etc., and separates the injection needle mounting component from the cartridge holder.

Here, the convex part is formed on the side of the first connector connected to the cartridge holder, rather than on the second connector side in the main body part. That is, the convex part is provided at a portion that is closer to the connection between the cartridge holder and the injection needle mounting component than the second connector. Accordingly, when pressure is applied to the convex part, the force that disconnects the cartridge holder from the injection needle mounting component is readily transmitted through the convex part to the connected portion. Consequently, the user can apply pressure to the convex part and easily pull the injection needle mounting component away from the cartridge holder.

Preferably, the outside diameter of the convex part is less than the outside diameter of the first connector, and greater than the outside diameter of the second connector.

With the above configuration, since the outside diameter of the convex part is less than the outside diameter of the first connector, the convex part tends not to get in the way when the injection needle mounting component is connected to the cartridge holder. Also, the outside diameter of the convex part is greater than that of the second connector. Thus, the second connector does not interfere when the injection needle mounting component is pulled away from the cartridge holder, and the user can easily operate the convex part with a tool, a hand, etc.

Preferably, the convex part has a polyhedral external shape as seen in the insertion direction of the injection needle component.

With the above configuration, the convex part has a polyhedral shape as seen in the insertion direction of the injection needle component. Thus, the convex part can be easily operated, such as being pulled, turned, etc., by grasping two opposing sides of the polyhedron with a tool, a hand, etc., for example.

Preferably, the convex part has a regular hexagonal external shape as seen in the insertion direction of the injection needle component.

With the above configuration, the convex part has a regular hexagonal external shape as seen in the insertion direction of the injection needle component, so the convex part can be easily operated grasping two opposing sides of the regular hexagon with a tool, a hand, etc., for example. In particular, the convex part can be easily operated with a commercially available tool such as a hexagonal socket wrench.

Preferably, the injection needle mounting component is provided to the end of the main body case.

With the above configuration, the injection needle mounting component is provided to the end of the main body case. The injection needle mounting component is fixed to the cartridge holder by connecting the first connector of the injection needle mounting component to the holder-side connector of the cartridge holder. In this case, the convex part sticks out from the end of the main body case. If a problem occurs with the cartridge holder driver, etc., the user can easily operate the convex part sticking out from the end of the main body case with a tool, a hand, etc.

Preferably, a through-hole through which the pharmaceutical cartridge can pass is provided in the center of the convex part and the first connector.

With the above configuration, the injection needle mounting component can be mounted at the distal end of the cartridge holder by connecting the first connector of the injection needle mounting component to the holder-side connector. Then, the pharmaceutical cartridge is pressed toward the distal end of the cartridge holder, causing the distal end of the pharmaceutical cartridge to pass through the through-hole in the convex part and the first connector. In this state, let us assume that the cartridge holder cannot be opened in order to take out the pharmaceutical cartridge.

The user applies pressure to the convex part with a tool, a hand, etc., and thereby removes the injection needle mounting component from the cartridge holder. At this point, the pharmaceutical cartridge sticks out from the cartridge holder by the amount by which it was passed through the through-hole. The user can remove the pharmaceutical cartridge from the cartridge holder by grasping the protruding distal end of the pharmaceutical cartridge with a tool, a hand, etc., for example.

Preferably, the injection needle mounting member comprises a main body part, a convex part, and a first connector. The injection needle mounting member connects the injection needle component to the cartridge holder. The convex part sticks out past the outer surface of the main body part. The cartridge holder here has a holding space and a holder-side connector. The holding space is a space in which a pharmaceutical cartridge can be held. The holder-side connector is provided at the end of the holding space. The first connector is connected to the holder-side connector of the cartridge holder, and is formed continuously with the main body part.

When the above-mentioned injection needle mounting member is attached to the cartridge holder, the same action and effect can be obtained as with the above-mentioned pharmaceutical injection device. When this injection needle mounting member is applied to a pharmaceutical injection device, the injection needle mounting member is fixed to the cartridge holder. More specifically, the first connector of the injection needle mounting member is connected to the holder-side connector of the cartridge holder of the pharmaceutical injection device. At this point, since only the first connector is connected to the holder-side connector, the convex part sticks out past the outer surface of the cartridge holder. The user can pull the injection needle mounting member away from the cartridge holder by applying pressure to the convex part, such as by pulling or turning it with a tool, a hand, etc.

With certain implementations, a pharmaceutical cartridge can be taken out of the pharmaceutical injection device even if the pharmaceutical injection device cannot be automatically driven by electric drive.

DETAILED DESCRIPTION

The pharmaceutical injection device 100 pertaining to a first implementation will now be described.

First Embodiment

Figure 1:
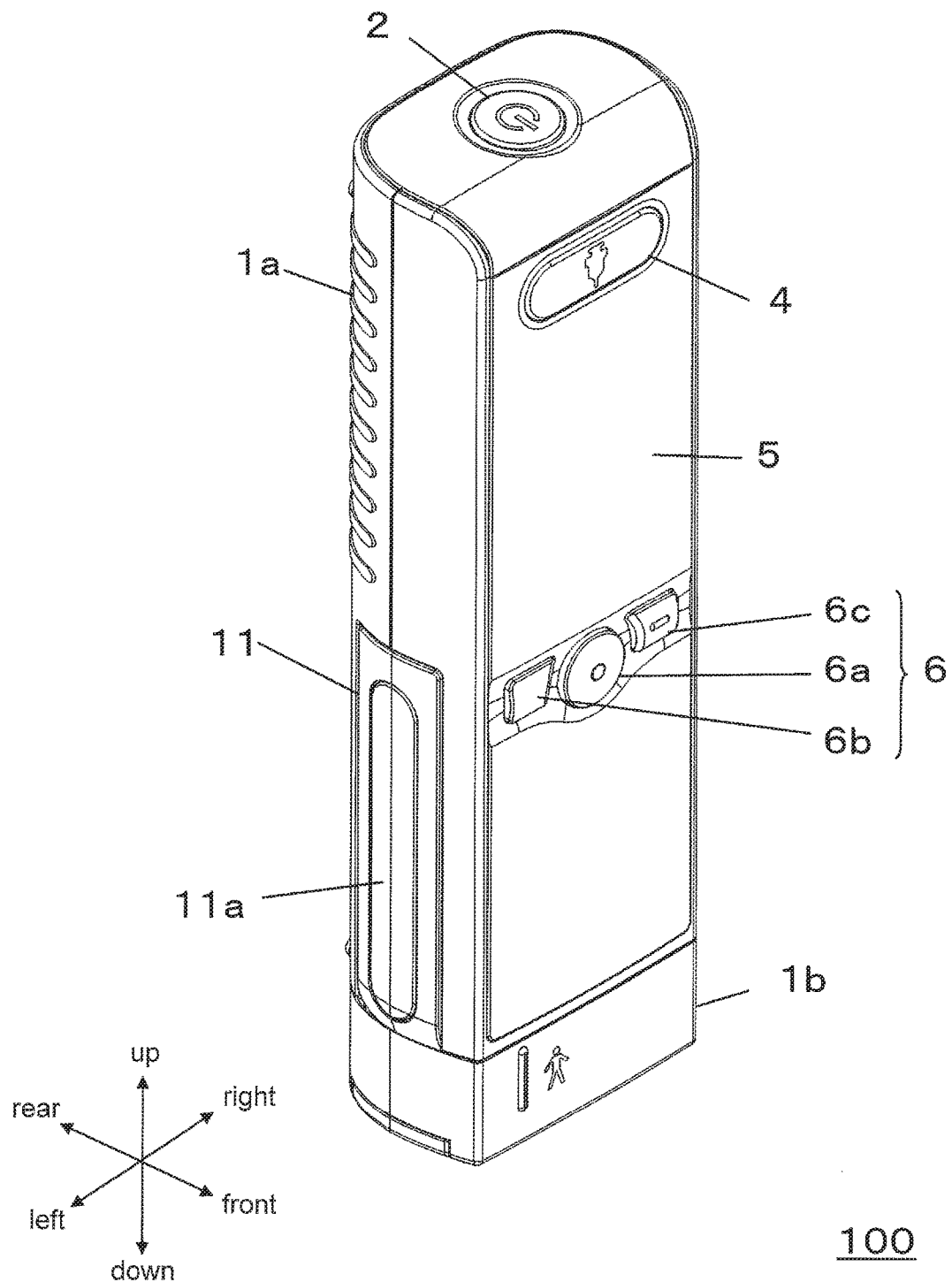
FIG. 1 is an oblique view of the outside of the pharmaceutical injection device pertaining to a first embodiment.
Figure 2:
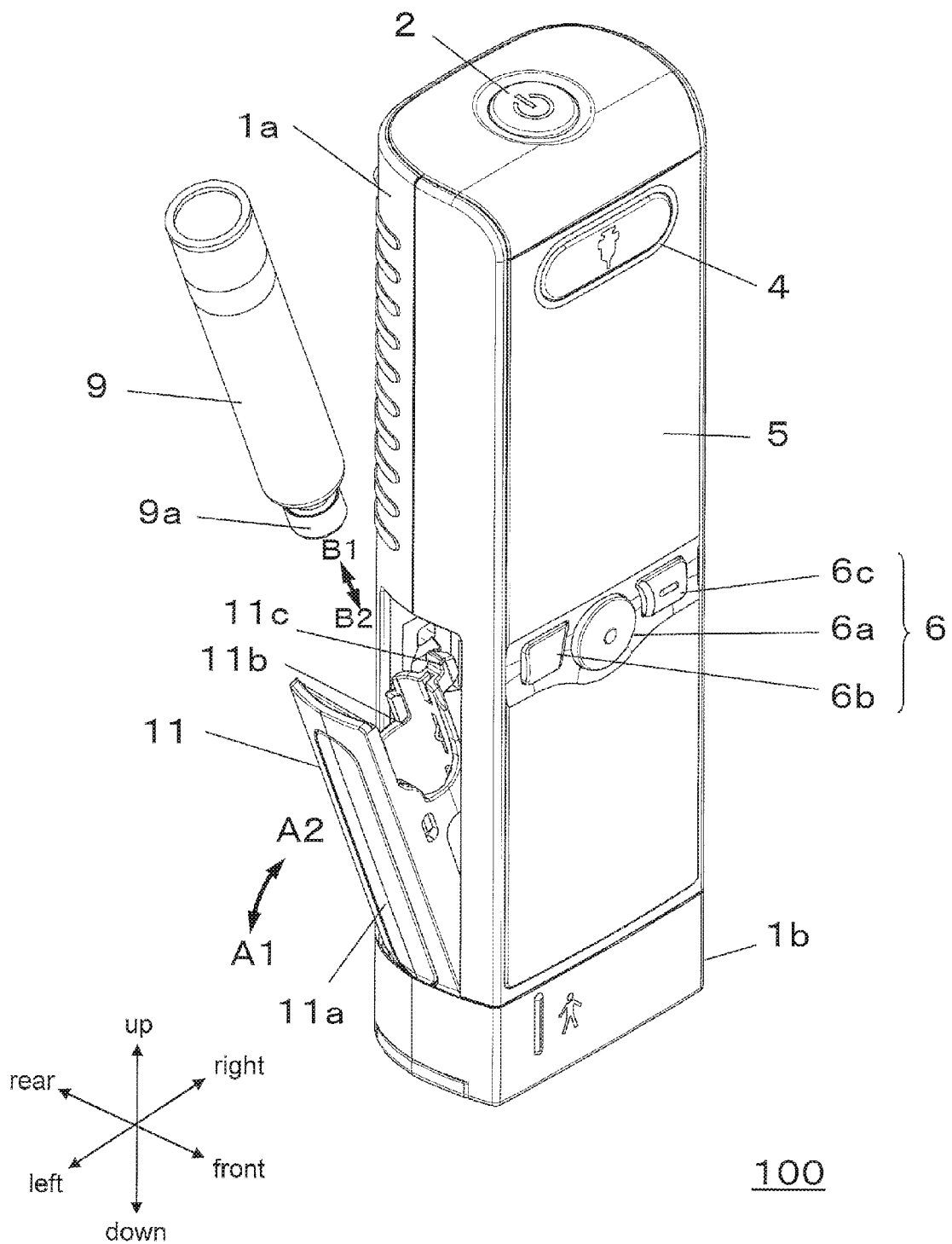
FIG. 2 is an oblique view of the open state of the cartridge holder of the pharmaceutical injection device in FIG. 1.
Figure 3A:
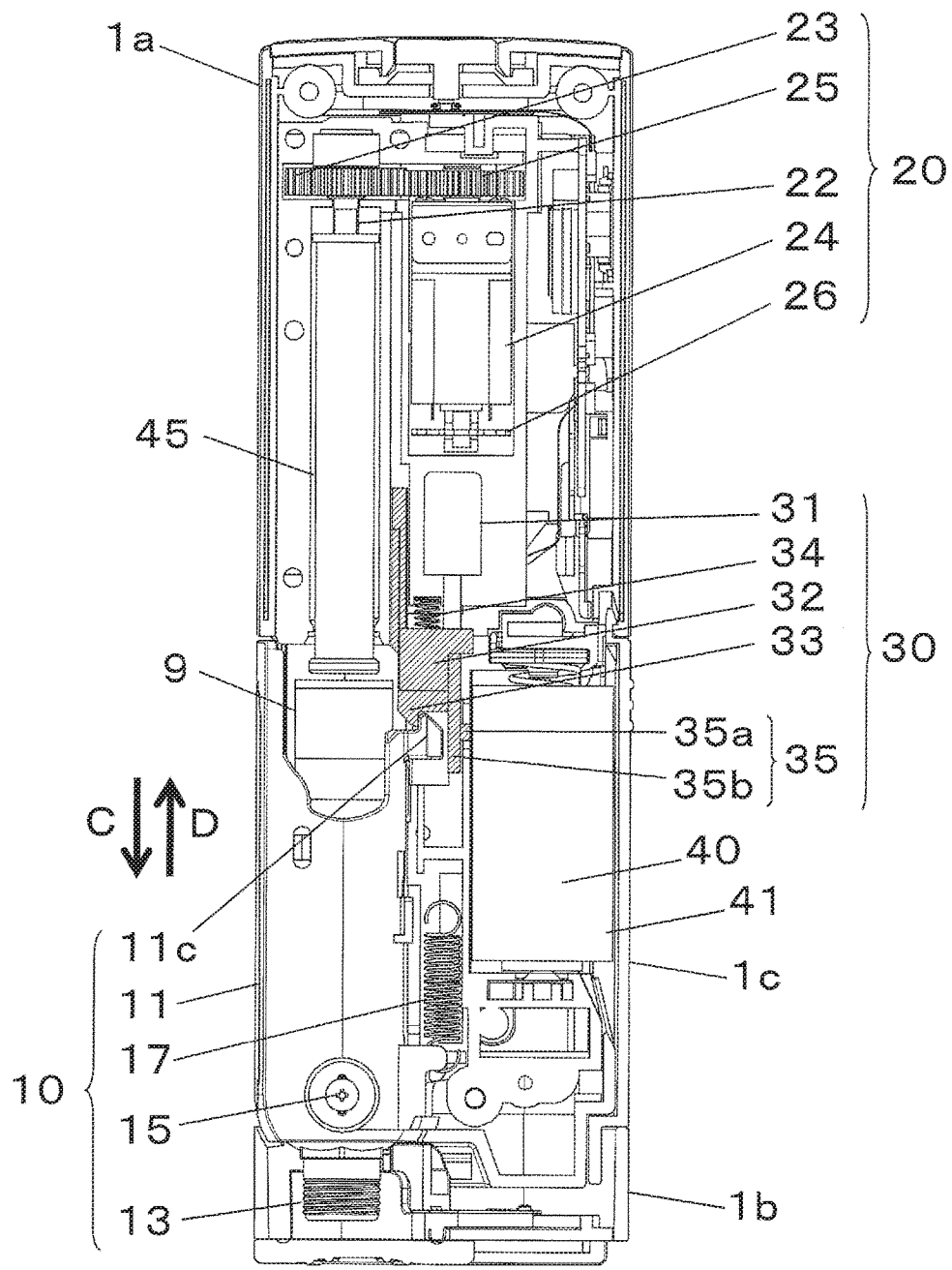
FIG. 3A is a front cross section showing the internal configuration of the pharmaceutical injection device in FIG. 1.
Figure 3B:
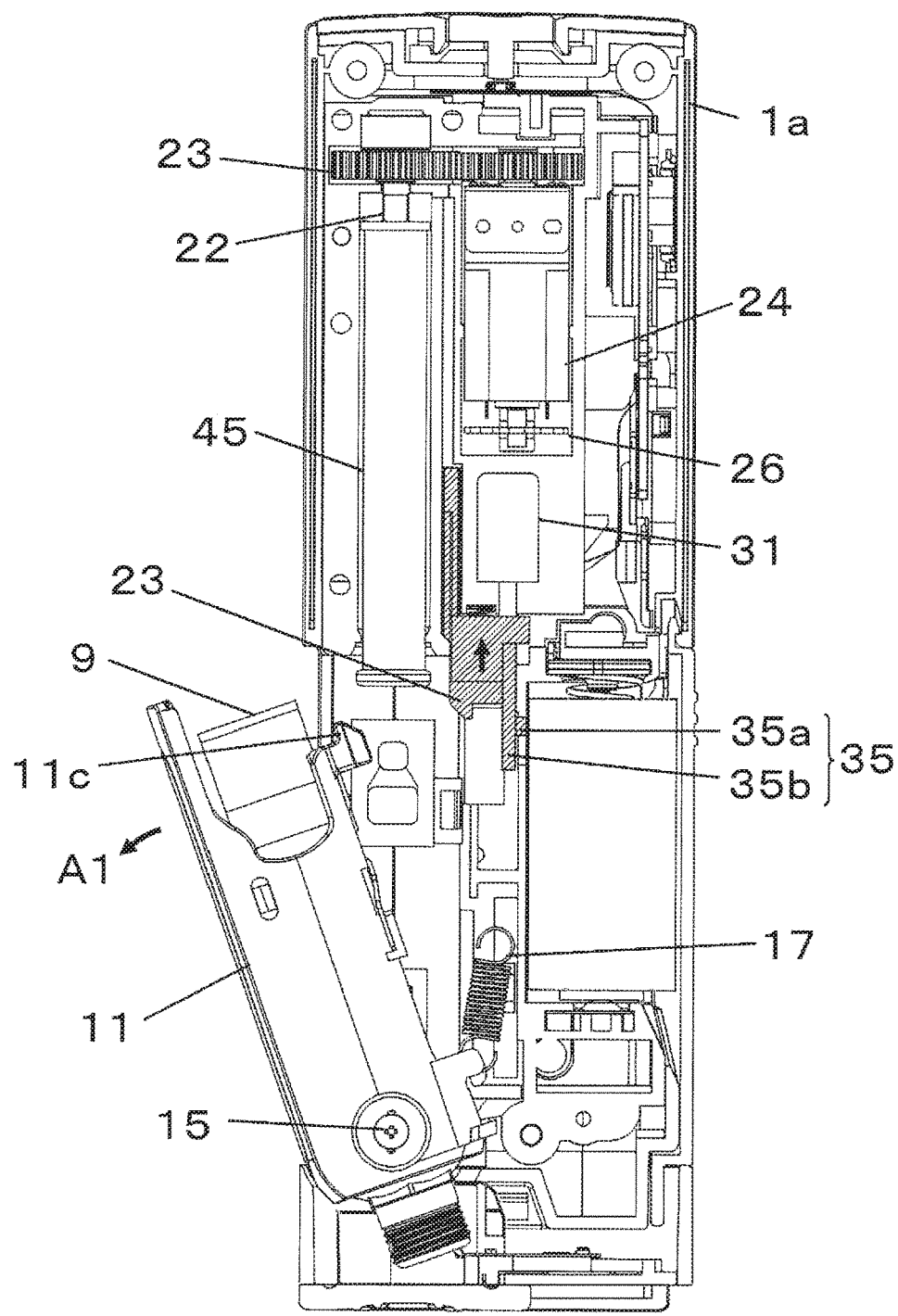
FIG. 3B is a front cross section showing the internal configuration when the cartridge holder of the pharmaceutical injection device is open.

FIG. 1 is an oblique view of the outside of the pharmaceutical injection device 100 pertaining to the first embodiment. FIG. 2 is an oblique view of the open state of a cartridge holder 11 of the pharmaceutical injection device 100 in FIG. 1. FIG. 3A is a front cross section showing the internal configuration of the pharmaceutical injection device 100 in FIG. 1. FIG. 3B is a front cross section showing the internal configuration when the cartridge holder 11 of the pharmaceutical injection device 100 is open.

In the following description, the "front," "rear," "left," "right," "up," and "down" directions correspond to the directions of the arrows shown in FIGS. 1 and 2, etc. That is, the side on which the pharmaceutical injection switch 4, display component 5, and setting switch 6 are provided is the "front," and the opposite side from the "front" is the "rear." The side on which the cartridge holder 11 (discussed below) is provided is the "left," and the opposite side from the "left" is the "right." The side on which a power switch 2 (discussed below) is provided is "up," and the opposite side from "up" on which a cap 1b (discussed below) is provided is "down."

First, the external configuration of the pharmaceutical injection device 100 will be described.

(1) External Configuration

As shown in FIGS. 1, 2, and 3A, the pharmaceutical injection device 100 pertaining to the first embodiment comprises a main body case 1a, the cap 1b, and a cover 1c (see FIG. 3A).

(1-1) Main Body Case 1a, Cap 1b, and Cover 1c

The main body case 1a is in the form of a slender tube, and is roughly hexagonal in its outer shape. The main body case 1a is designed to be long and wide enough to allow a user to grip it.

The cap 1b is removably mounted to the main body case 1a so as to cover the lower part of the main body case 1a. An injection needle mounting component 13 (discussed below) is provided to the lower part of the main body case 1a, and the cap 1b covers the area around the injection needle mounting component 13. This cap 1b is what comes into contact with the skin when the pharmaceutical is administered. However, if no skin contact portion is required, the cap 1b need not be provided to the main body case 1a. That is, the area around the injection needle mounting component 13 may be left exposed from the main body case 1a.

In this embodiment, the cartridge holder 11 (discussed below) is provided to the left-side portion of the main body case 1a as shown in FIGS. 1 and 2. The cover 1c (see FIG. 3A), which is used to open and close a power supply holding space 41 in which a power supply 40 is held, is provided to the right-side portion of the main body case 1a. That is, it is provided at a location that is opposite the cartridge holder 11, the power supply holding space 41 and the cover 1c. The positional relation of these components is not limited to what is given in this embodiment, and for example the cartridge holder 11 may be provided to the right-side portion, and the power supply holding space 41 and the cover 1c to the left-side portion. The layout of the other members in the interior of the main body case 1a can also vary according to this layout.

(1-2) Switches 2, 4, and 6 and Display Component 5

The power switch 2 is provided to the top face of the main body case 1a. The pharmaceutical injection switch 4, the display component 5, and the setting switch 6 are provided in that order, from top to bottom, to the front face portion of the main body case 1a.

For example, the pharmaceutical injection switch 4 is provided at the upper part of the front face portion of the main body case 1a. The setting switch 6 is provided in the approximate middle part of the front face portion of the main body case 1a, for example.

The setting switch 6 is used to set the pharmaceutical dose, and includes a middle switch 6a, a left switch 6b, and a right switch 6c. The middle switch 6a can be a switch for confirming the set dose, for example. The left switch 6b and the right switch 6c can be, for example, switches for adjusting how much to increase or decrease the dose, respectively.

The display component 5 is provided above the setting switch 6 on the front face portion of the main body case 1a so as to make it easy to check the settings made with the setting switch 6. The display component 5 can be, for example, an LCD (liquid crystal display) panel, an organic EL (electro-luminescence) panel, or another such display device.

(2) Internal Configuration

Next, the internal configuration of the pharmaceutical injection device 100 will be described.

As shown in FIG. 3A, the pharmaceutical injection device 100 includes, for example, a cartridge holder mechanism 10, a piston drive mechanism 20, a takeout mechanism 30, the power supply 40, and a piston 45.

(2-1) Power Supply 40

The power supply 40 is a member capable of generating electricity, such as a battery.

As shown in FIG. 3A, the power supply holding space 41, in which the power supply 40 can be held, is provided in the interior of the main body case 1a. The cover 1c is also provided to open and close the power supply holding space 41.

The power supply 40 can be installed in and removed from the power supply holding space 41. Thus, when there is no more charge in the power supply 40, the user can remove the cover 1c, take the used power supply 40 out of the power supply holding space 41, and put in a fresh power supply 40.

The power generated by the power supply 40 is supplied to a driver 31, a piston drive force generator 24, a controller 50, and so forth (discussed below).

The power supply 40 may be a member to which power is supplied from a separate power supply through a cable or the like.

(2-2) Piston 45

As shown in FIGS. 3A and 3B, the piston 45 is a cylindrical body that is hollow inside. The piston 45 is provided above the cartridge holder 11 in the main body case 1a. The piston 45 is pulled out of a pharmaceutical cartridge 9 or inserted into the pharmaceutical cartridge 9 held in the cartridge holder 11.

More specifically, when the piston 45 moves downward and is inserted into the pharmaceutical cartridge 9, the pharmaceutical inside the pharmaceutical cartridge 9 is either discharged or administered to the patient, etc. On the other hand, when the piston 45 moves upward, it is pulled out of the pharmaceutical cartridge 9, so the pharmaceutical cartridge 9 can be replaced.

(2-3) Cartridge Holder Mechanism 10 and Takeout Mechanism 30

As shown in FIGS. 3A, 3B, etc., the cartridge holder mechanism 10 includes the cartridge holder 11, the injection needle mounting component 13, a fulcrum 15, and a removal spring 17. The takeout mechanism 30 includes the driver 31, a latching receiver main body 32, a latching receiver 33, a drive spring 34, and a manipulation component 35.

(a) Cartridge Holder 11

As shown in FIGS. 1 and 2, the cartridge holder 11 is a member that can be held in the interior of the main body case 1a, and is provided openably and closeably with respect to the main body case 1a.

The cartridge holder 11 has an outer wall 11a, a holding space 11b, and a holder latching component 11c.

The outer wall 11a is flush with the outer surface of the main body case 1a when the cartridge holder 11 is closed and held inside the main body case 1a.

The holding space 11b of the cartridge holder 11 is a space in which a cylindrical pharmaceutical cartridge 9 is held, for example. The pharmaceutical that is to be administered by the pharmaceutical injection device 100 is sealed inside the pharmaceutical cartridge 9.

The holder latching component 11c latches the latching receiver 33 of the takeout mechanism 30 (discussed below). When the cartridge holder 11 is closed and the holder latching component 11c latches the latching receiver 33, the cartridge holder 11 is housed inside the main body case 1a. Here, the cartridge holder 11 held in the main body case 1a is subjected by the removal spring 17 (discussed below) to a biasing force in the direction of being open. Thus, the holder latching component 11c keeps the cartridge holder 11 in a state of being closed with respect to the main body case 1a, against the biasing force of the removal spring 17. The holder latching component 11c is formed so as to stick out to the latching receiver 33 side, so as to allow latching to the latching receiver 33.

(b) Fulcrum 15

The fulcrum 15 is provided to the lower end of the cartridge holder 11. The cartridge holder 11 is attached to the main body case 1a via the fulcrum 15. The cartridge holder 11 pivots around this fulcrum 15, allowing the cartridge holder 11 to be opened and closed with respect to the main body case 1a.

(c) Removal Spring 17

The removal spring 17 connects the cartridge holder 11 and the main body case 1a. The removal spring 17 is disposed so that when the cartridge holder 11 is in a closed state (see FIG. 3A), a biasing force is exerted in the direction of putting the cartridge holder 11 in an open state (see FIG. 3B).

(d) Latching Receiver Main Body 32 and Latching Receiver 33

The latching receiver main body 32 is the base on which the latching receiver 33 is provided. The latching receiver 33 is integrally provided to the latching receiver main body 32. When the cartridge holder 11 is held inside the main body case 1a, the holder latching component 11c latches the latching receiver 33. The latching receiver 33 is formed so as to stick out to the holder latching component 11c side so as to allow latching of the holder latching component 11c.

(e) Driver 31 and Drive Spring 34

The drive spring 34 is attached to the latching receiver main body 32 so as to bias the latching receiver 33 downward, that is, so as to bias the latching receiver 33 toward the holder latching component 11c side of the cartridge holder 11. For example, as shown in FIG. 3A, the drive spring 34 is disposed on the opposite side from the side where the holder latching component 11c and the latching receiver 33 are provided. That is, the drive spring 34 is disposed so as to be opposite the holder latching component 11c and the latching receiver 33.

The driver 31 generates a force that pulls the latching receiver 33 upward, that is, in the direction in which the latching receiver 33 moves away from the holder latching component 11c. Thus, the latching receiver 33 moves up and down under the action of the driver 31 and the drive spring 34. A solenoid is an example of the driver 31.

To describe this in more specific terms, the latching receiver 33 is usually located down, that is, on the cartridge holder 11 side, by the biasing force of the drive spring 34. The latching receiver 33 is located up, that is, at a place away from the cartridge holder 11, only when pulled by the driver 31. The lower position of the latching receiver 33 here is the position at which the holder latching component 11c latches the latching receiver 33. The upper position of the latching receiver 33 is the position at which the holder latching component 11c is unlatched from the latching receiver 33.

Next, the operation of the driver 31 and the drive spring 34 when the pharmaceutical cartridge 9 is replaced will be described.

When the pharmaceutical cartridge 9 is replaced, the user operates a specific switch or the like to open the cartridge holder 11. The driver 31 receives the operation of the switch, etc., and pulls the latching receiver main body 32, the latching receiver 33, etc., upward. Consequently, the holder latching component 11c moves away from the latching receiver 33, and the holder latching component 11c is automatically unlatched from the latching receiver 33. The cartridge holder 11 then rotates around the fulcrum 15 under the biasing force of the removal spring 17, and opens toward the outside of the main body case 1a (the direction of the arrow A1 in FIG. 2).

The user then takes the old pharmaceutical cartridge 9 out of the holding space 11b of the cartridge holder 11 as indicated by the arrow B1. The user then inserts a fresh pharmaceutical cartridge 9 as indicated by the arrow B2.

After this, the user operates a specific switch or the like to close the cartridge holder 11. Consequently, the driver 31 halts the upward pulling of the latching receiver main body 32, the latching receiver 33, etc. The latching receiver 33 then moves downward under the biasing force of the drive spring 34.

The user then closes the cartridge holder 11 toward the inside of the main body case 1a (the direction of the arrow A2 in FIG. 2), and the holder latching component 11c latches the latching receiver 33. The above operation results in the fresh pharmaceutical cartridge 9 being installed in the main body case 1a as shown in FIG. 3A.

In the above description, it is assumed that the driver 31 halts the upward pulling of the latching receiver main body 32, the latching receiver 33, and so forth when the user has operated a specific switch, etc. However, the driver 31 may instead halt the upward pulling of the latching receiver main body 32, the latching receiver 33, and so forth after a specific length of time has elapsed. Alternatively, the driver 31 may stop pulling after it has been detected by a detection means (not shown) that the cartridge holder 11 is open.

(f) Manipulation Component 35

Figure 4:
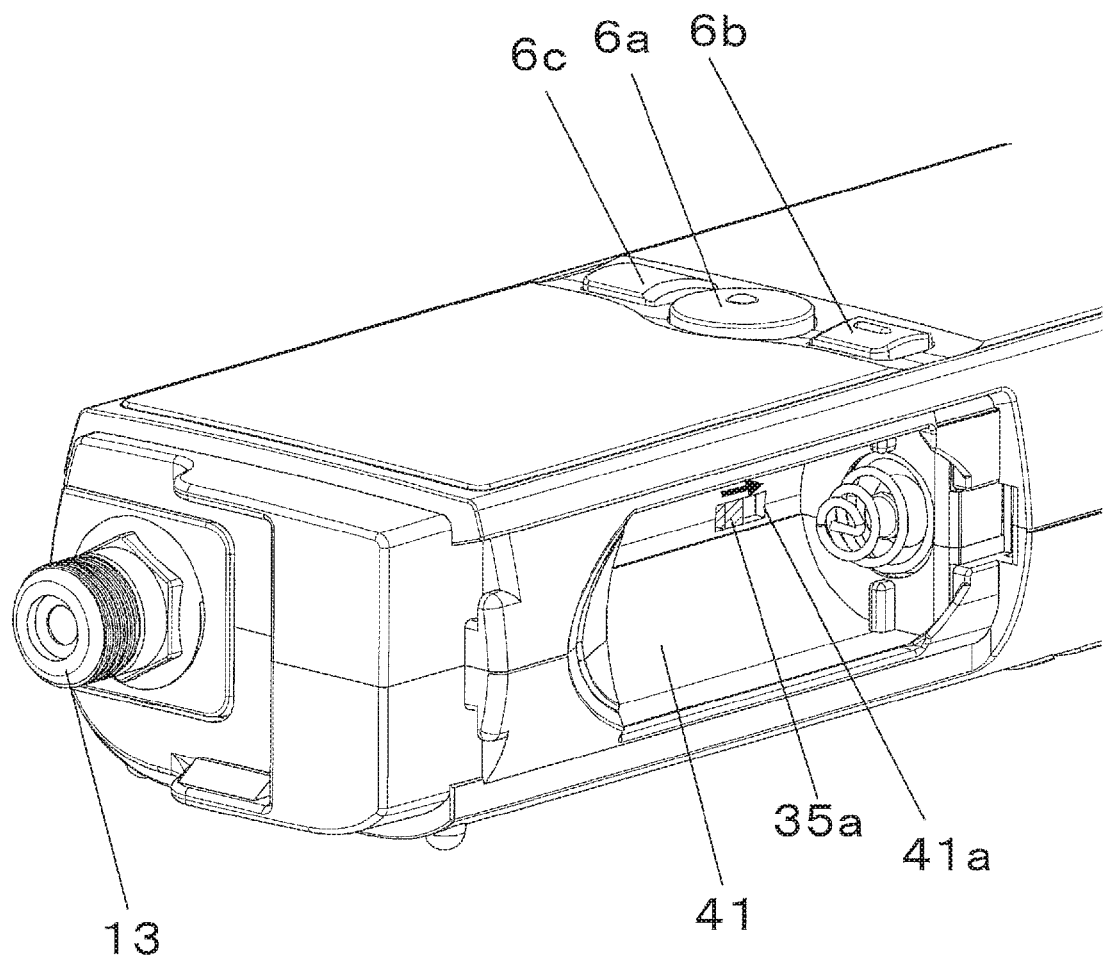
FIG. 4 shows the state when a cover and the power supply have been removed from the main body case of the pharmaceutical injection device.

FIG. 4 shows the state when the cover 1c and the power supply 40 have been removed from the main body case 1a of the pharmaceutical injection device 100.

As shown in FIGS. 3A and 3B, the manipulation component 35 is integrally attached to the latching receiver main body 32 and the latching receiver 33. The manipulation component 35 is manually operated by the user, and the latching receiver main body 32 and the latching receiver 33 are moved in response to this manipulation.

The manipulation component 35 has a protrusion 35a and a protrusion placement part 35b. The protrusion placement part 35b is a member that serves as the base for the protrusion 35a. The protrusion 35a is provided so as to stick out from the protrusion placement part 35b. As shown in FIG. 4, the protrusion 35a is provided so as to be exposed through an opening 41a in the power supply holding space 41. Thus, the user can manually operate the protrusion 35a by removing the power supply 40 from the power supply holding space 41. Also, since the protrusion 35a is provided in the opening 41a of the main body case 1a, this prevents the protrusion 35a from being accidentally operated by contact with the user's hand, another member, or the like.

When the user slides the protrusion 35a up with his finger, the latching receiver 33 also moves upward. Thus, the holder latching component 11c moves away from the latching receiver 33, and the latching receiver 33 is manually unlatched from the holder latching component 11c. Thus, the user can manipulate the protrusion 35a to manually open the cartridge holder 11.

That is, with the above embodiment, the latching receiver 33 of the takeout mechanism 30 can be automatically driven by the driver 31 under electrical power, or can be moved manually without any electrical power.

For example, there are situations when problems occur with the power supply, and the latching receiver 33 of the takeout mechanism 30 cannot be electrically driven. If this should happen, the user can manually operate the protrusion 35a, thereby manually moving the latching receiver 33 without any electrical power, and unlatching the latching receiver 33 from the holder latching component 11c. Thus, the user can open the cartridge holder 11 and take out the pharmaceutical cartridge 9.

Here, the size of the opening 41a is large enough to allow the latching receiver 33 to be unlatched from the holder latching component 11c by moving the protrusion 35a within the opening 41a. That is, the opening 41a defines the range over which the protrusion 35a can move. This allows the user to smoothly move the protrusion 35a within the range of the opening 41a. This movement of the protrusion 35a then allows the latching receiver 33 and the holder latching component 11c to be manually unlatched.

The manipulation component 35 has the protrusion 35a that sticks out from the protrusion placement part 35b, so the manipulation component 35 can be easily manipulated by the user by hooking it with a finger, etc. This operation of the protrusion 35a affords easy operation of the latching receiver 33.

As discussed above, the holder latching component 11c is formed so as to stick out on the latching receiver 33 side. Meanwhile, the latching receiver 33 is formed so as to stick out on the holder latching component 11c side. That is, in a state in which the cartridge holder 11 is held in the main body case 1a, the holder latching component 11c protrudes upward, and the latching receiver 33 protrudes downward.

Thus, the protrusion direction of the holder latching component 11c and the latching receiver 33 in the up and down direction follows the up and down direction in which the protrusion 35a moves. That is, the direction in which the latching receiver 33 moves away from the holder latching component 11c is along the direction in which the latching receiver 33 is slid. Therefore, the holder latching component 11c can be manually unlatched from the latching receiver 33 by manually applying pressure to and moving the latching receiver 33.

In the above description, the protrusion 35a is provided to the opening 41a inside the main body case 1a. However, the protrusion 35a may instead be provided to an opening in the outer wall of the main body case 1a. Here again, because it is provided to an opening in the outer wall of the main body case 1a, the protrusion 35a can be prevented from being unintentionally operated by contact with the user's hand, another member, or the like.

In the above description, the protrusion 35a moves up and down when manipulated by the user. However, the latching receiver 33 may be unlatched from the holder latching component 11c by moving the protrusion 35a to the left and right.

In addition, the user may unlatch the latching receiver 33 from the holder latching component 11c by moving the protrusion 35a deeper into the opening 41a. In this case, when the user moves the protrusion 35a deeper into the opening 41a, for example, the holder latching component 11c is pushed and the latching receiver 33 is manually unlatched from the holder latching component 11c.

The protrusion 35a and the protrusion placement part 35b may be formed integrally, or they may be separate and linked together. Also, the manipulation component 35 may be formed integrally with the latching receiver main body 32 and the latching receiver 33, or these may be separate and linked together.

(g) Injection Needle Mounting Component 13

Figure 5:
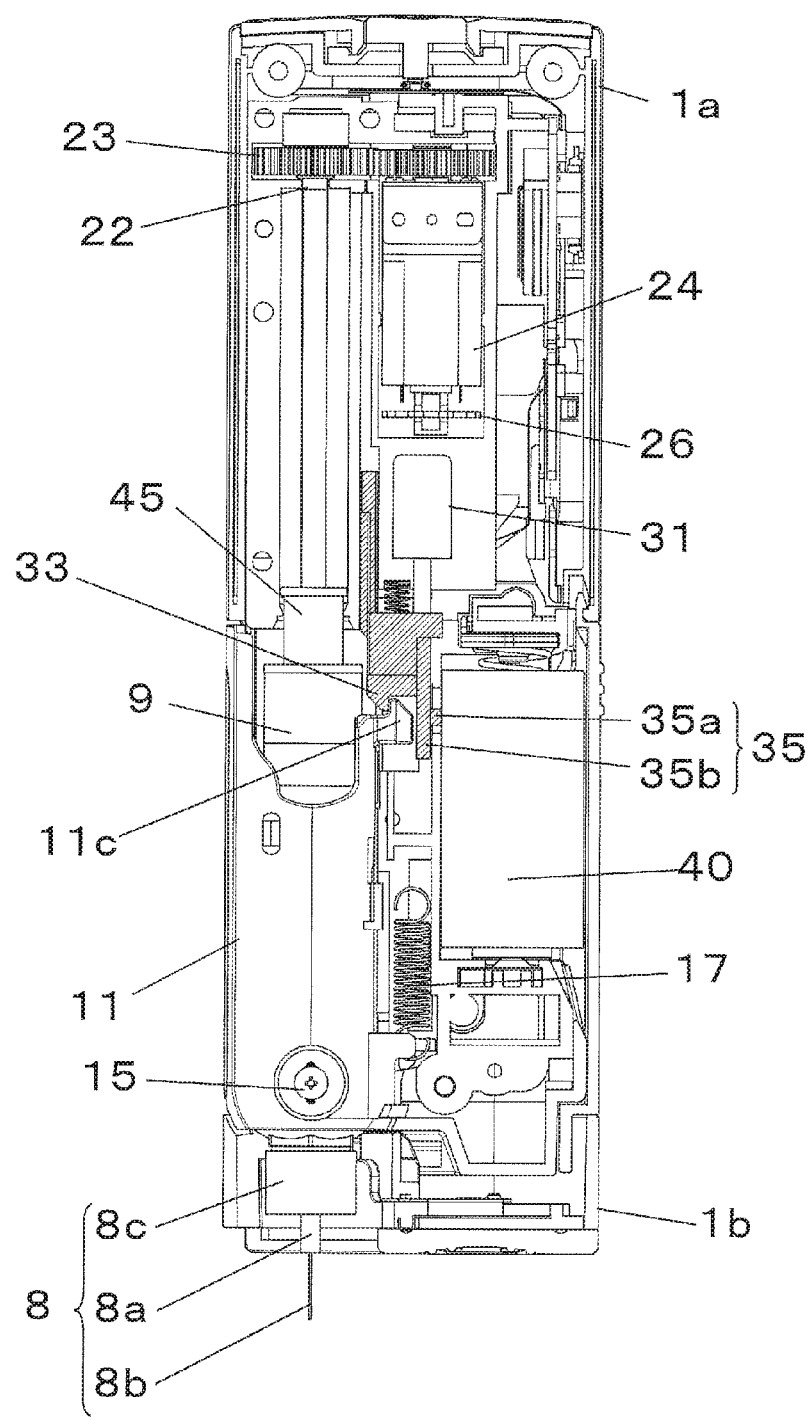
FIG. 5 shows the state when an injection needle component has been mounted to the injection needle mounting component of the pharmaceutical injection device.

FIG. 5 shows the state when an injection needle component 8 has been mounted to the injection needle mounting component 13 of the pharmaceutical injection device 100.

The injection needle mounting component 13 is a substantially cylindrical member, and is used to connect the injection needle component 8 to the cartridge holder 11. The injection needle mounting component 13 is provided to the lower portion of the cartridge holder 11, that is, to its end. The pharmaceutical cartridge 9 is inserted from above the injection needle mounting component 13, and the distal end 9a (FIG. 2) of the pharmaceutical cartridge 9 is located inside the injection needle mounting component 13. Meanwhile, the injection needle component 8 is inserted from below the injection needle mounting component 13. Here, the injection needle component 8 includes an injection needle base 8a (the base of the needle 8b), a hollow needle 8b, and an attachment member 8c. The attachment member 8c is used to connect the injection needle mounting component 13 and the injection needle component 8. When the attachment member 8c is attached to the injection needle mounting component 13, the needle 8b passes into the interior of the pharmaceutical cartridge 9, allowing the pharmaceutical in the pharmaceutical cartridge 9 to be administered.

(2-4) Piston Drive Mechanism 20

As shown in FIG. 3A, the piston drive mechanism 20 is used to drive the piston 45, and includes a feed screw 22, a gear 23, the piston drive force generator 24, a drive gear 25, and an encoder 26.

The piston drive mechanism 20 drives the piston 45 so that the piston 45 is inserted into the pharmaceutical cartridge 9 or pulled out of the pharmaceutical cartridge 9. The piston 45 moves downward when the pharmaceutical in the pharmaceutical cartridge 9 is discharged or administered, and moves upward when the pharmaceutical cartridge 9 is replaced.

To describe this in more detail, the piston drive force generator 24 generates a drive force for moving the piston 45. The piston drive force generator 24 is, for example, a motor or another such power source. The piston drive force generator 24 (motor) has its drive shaft disposed substantially parallel to the movement direction of the piston 45, that is, the up and down direction. The drive gear 25, which is linked to the drive shaft of the piston drive force generator 24, is provided on the upper side of the piston drive force generator 24.

A threaded hole is formed at the upper end of the piston 45, and the feed screw 22 is threaded into this hole. The feed screw 22 is fixed to the gear 23, which is provided above the piston 45. The gear 23 meshes with the drive gear 25.

When the piston drive force generator 24 rotates, its rotational force is transmitted through the drive gear 25 and the gear 23 to the feed screw 22, causing the feed screw 22 to rotate. This rotation of the feed screw 22 causes the piston 45 to move downward (the arrow C direction in FIG. 3A) or upward (the arrow D direction in FIG. 3A). When the piston 45 moves downward (the arrow C direction in FIG. 3A), it is inserted into the pharmaceutical cartridge 9. On the other hand, when the piston 45 moves upward (the arrow D direction in FIG. 3A), it is pulled out of the pharmaceutical cartridge 9.

The encoder 26 is connected to the piston drive force generator 24. The encoder 26 outputs electrical pulses according to the amount of rotation of the piston drive force generator 24 (motor). The encoder 26 sends these electrical pulses to the controller 50 (discussed below). The controller 50 can calculate the amount of movement of the piston 45 on the basis of the electrical pulses from the encoder 26.

(3) Control Block Configuration

Figure 6:
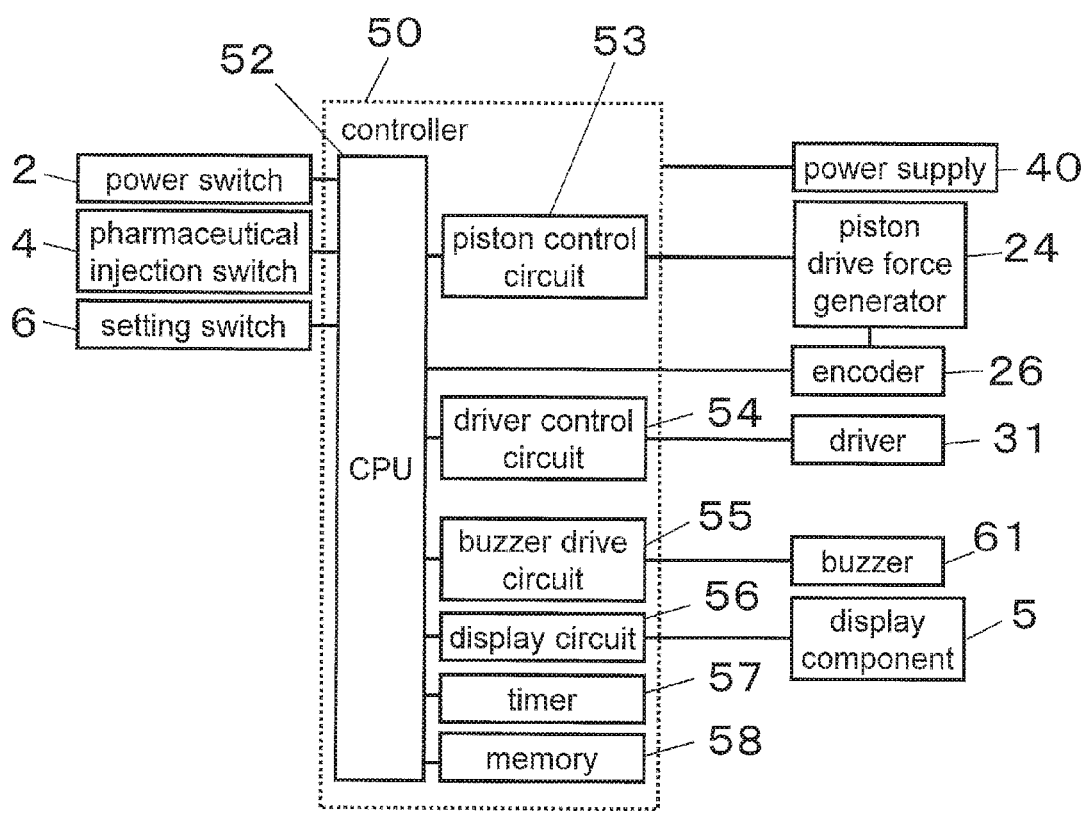
FIG. 6 is a control block diagram of the relation between the controller of the pharmaceutical injection device and the various members connected to the controller.

FIG. 6 is a control block diagram of the relation between the controller 50 of the pharmaceutical injection device 100 and the various members connected to the controller 50.

The pharmaceutical injection device 100 includes the controller 50, the power supply 40 that is connected to the controller 50, the piston drive force generator 24, the encoder 26, the driver 31, a buzzer 61, the display component 5, and the switches 2, 4, and 6.

The controller 50 performs various kinds of computation in order to control the pharmaceutical injection device 100 in various ways. The controller 50 has a CPU (central processing unit) 52 and various I/O interfaces and drive systems. The CPU 52 is connected to the various I/O interfaces and drive systems, and controls these. Examples of the various I/O interfaces and drive systems include a piston control circuit 53, a driver control circuit 54, a buzzer drive circuit 55, a display circuit 56, a timer 57, and a memory 58.

More specifically, the CPU 52 is connected to the power switch 2, the pharmaceutical injection switch 4, the setting switch 6, etc., and checks the input to these switches.

The piston control circuit 53 is used to drive the piston drive force generator 24 in order to generate drive force for moving the piston 45. The CPU 52 controls the piston drive force generator 24 via the piston control circuit 53. The encoder 26 is connected to the piston drive force generator 24. The encoder 26 outputs electrical pulses according to the drive of the piston drive force generator 24, and these are inputted to the CPU 52. The CPU 52 estimates the amount of movement of the piston 45 on the basis of these electrical signals inputted from the encoder 26.

The driver control circuit 54 is used to drive the driver 31 (a solenoid or the like). The CPU 52 controls the driver 31 via the driver control circuit 54.

The buzzer drive circuit 55 is used to drive the buzzer 61, which is used to inform the user with sound. The CPU 52 controls the buzzer 61 via the buzzer drive circuit 55.

The display circuit 56 is used to control the display component 5. The CPU 52 causes the display component 5 to give various displays via the display circuit 56.

The timer 57 manages the time. The memory 58 records information about pharmaceutical administration, information about the device operation, and so on.

The pharmaceutical injection device 100 pertaining to another implementation will now be described.

Second Embodiment

In the second embodiment the problem that is solved is that the piston 45 cannot be taken out of the pharmaceutical cartridge 9 based on the operation of the controller 50 in a state in which the piston 45 has been inserted into the pharmaceutical cartridge 9.

Accordingly, when a piston return switch 70 is operated, the piston drive force generator 24 is directly connected to the power supply 40. There are two ways to accomplish this, for example.

In the first method, the power supply 40 is connected to both the controller 50 and the piston drive force generator 24 while the controller 50 is still connected to the piston drive force generator 24.

In the second method, the controller 50 is disconnected from the piston drive force generator 24, and then the power supply 40 is connected to both the controller 50 and the piston drive force generator 24.

The first and second methods will now be described.

(1) First Method

Figure 7:
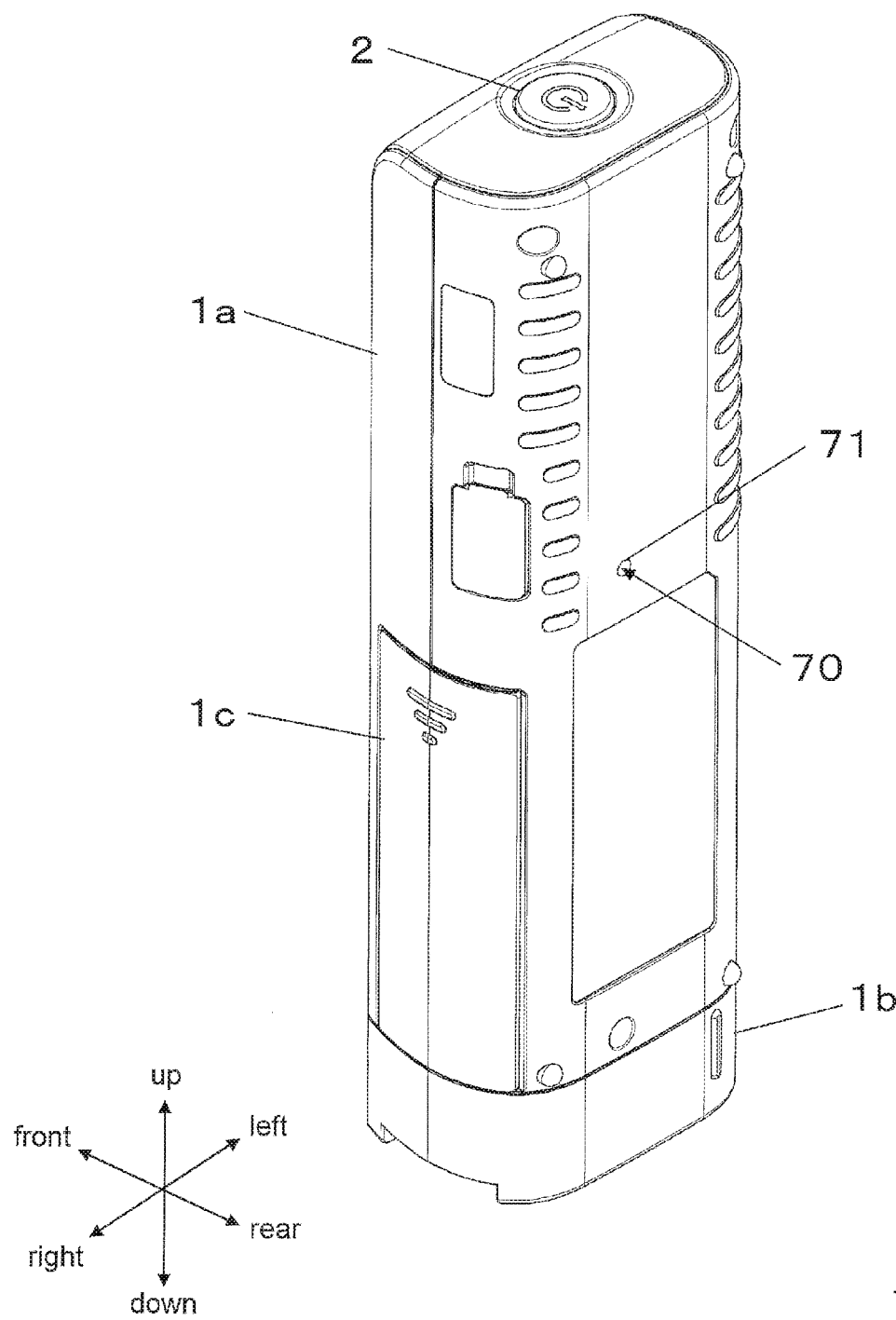
FIG. 7 is an oblique view of the exterior of the rear face of the pharmaceutical injection device pertaining to a second embodiment.
Figure 8:
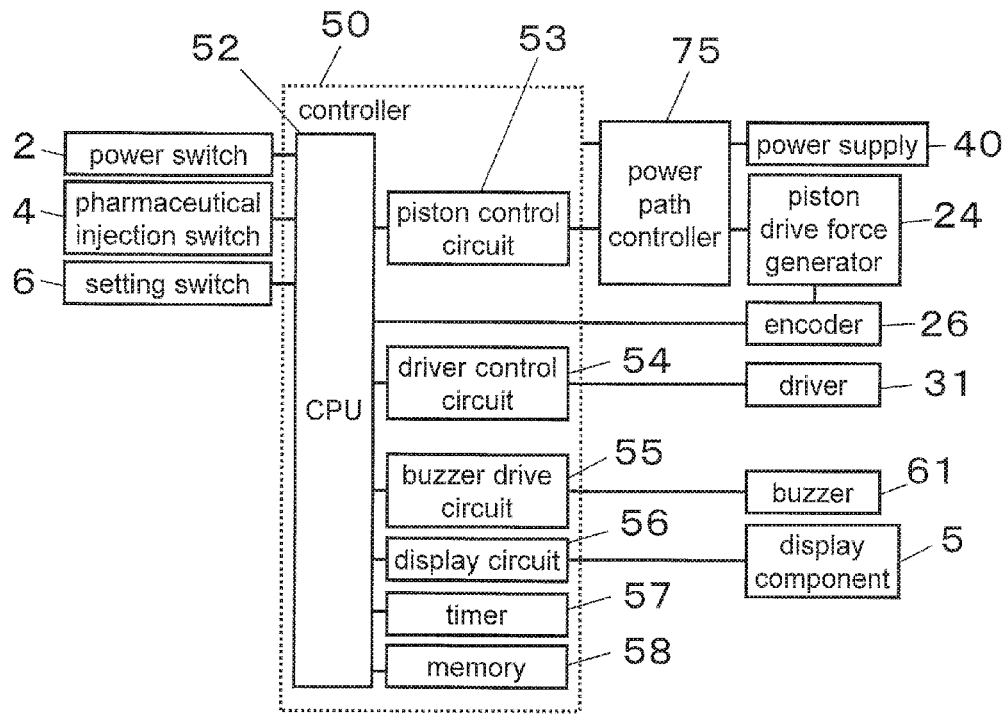
FIG. 8 is a control block diagram of the relation between the controller of the pharmaceutical injection device in FIG. 7 and the various members connected to the controller.
Figure 9A:
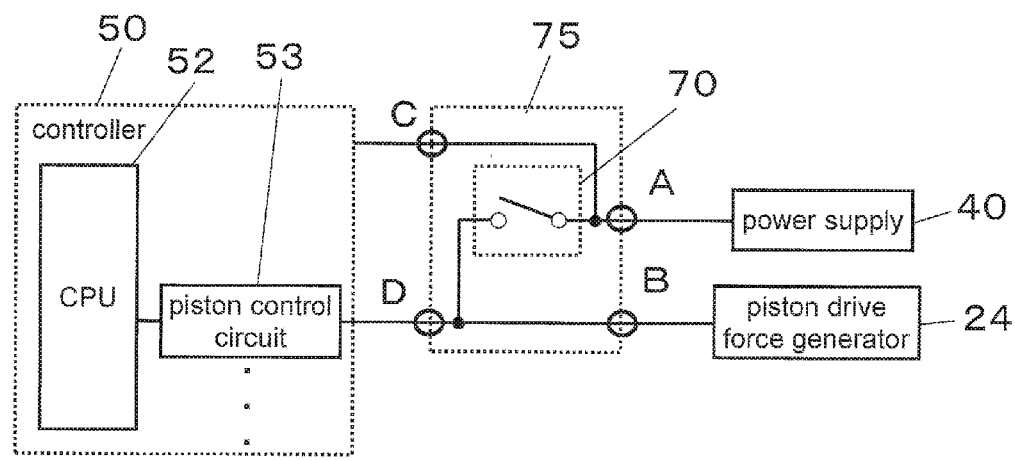
FIG. 9A shows the power path when a piston return switch has not been pressed in a first method.
Figure 9B:
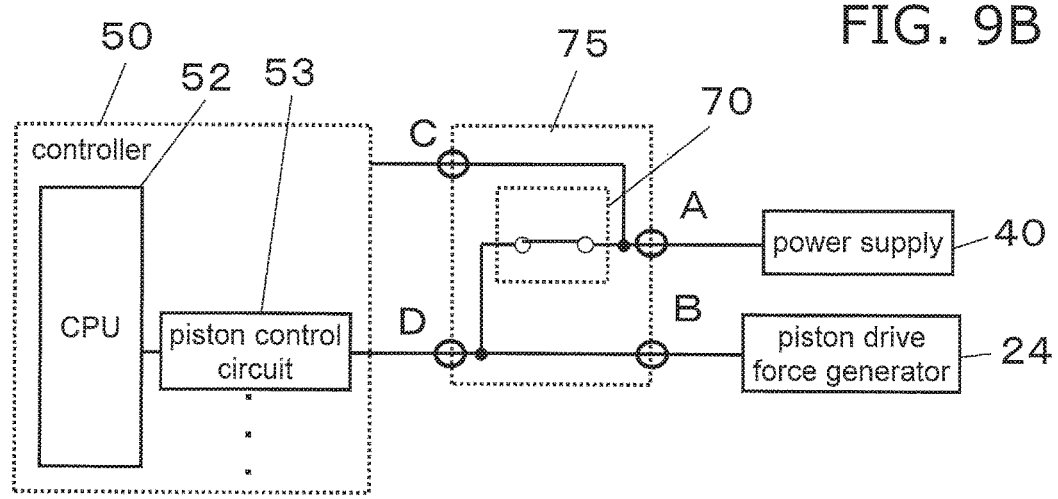
FIG. 9B shows the power path when the piston return switch has been pressed in the first method.

FIG. 7 is an oblique view of the exterior of the rear face of the pharmaceutical injection device pertaining to a second embodiment. FIG. 8 is a control block diagram of the relation between the controller 50 of the pharmaceutical injection device 200 in FIG. 7 and the various members connected to the controller 50. FIG. 9A shows the power path when the piston return switch 70 has not been pressed in the first method. FIG. 9B shows the power path when the piston return switch 70 has been pressed in the first method. Those components that are the same as in the first embodiment will be numbered the same, and their description will be either omitted or simplified.

This embodiment differs from the first embodiment in that the pharmaceutical injection device 200 has the piston return switch 70 (FIG. 7) and a power path controller 75 (FIG. 8).

The piston return switch 70 receives a command to pull the piston 45 inserted into the interior of the pharmaceutical cartridge 9 out of the pharmaceutical cartridge 9. A hole 71 is provided to the rear face of the main body case 1a. The piston return switch 70 is provided in the interior of this hole 71. Also, the piston return switch 70 is a push-button type of switch. The hole 71 is a tiny hole, for example, and the user can use a slender pin or the like to push the piston return switch 70 through the hole 71.

The power path controller 75 produces a power path according to whether or not the piston return switch 70 is operated. As shown in FIGS. 9A and 9B, the power path controller 75 is provided between the controller 50 and, the piston drive force generator 24 and power supply 40. The piston return switch 70 is provided inside the power path controller 75.

The power path controller 75 has, for example, four terminals A, B, C, and D. The terminal A is connected to the power supply 40. The terminal B is connected to the piston drive force generator 24. The terminal C is connected to the controller 50. The terminal D is connected to the piston control circuit 53. Inside the power path controller 75, the terminals A and C are linked, and the terminals B and D are linked, regardless of whether or not the piston return switch 70 is operated.

The power path when the piston return switch 70 has not been operated is as shown in FIG. 9A. In this case, since the piston return switch 70 has not been operated, the piston return switch 70 is in the open state shown in FIG. 9A. At this point the terminals A and B are not connected. Thus, the power supply 40 is connected to only the controller 50, and the piston drive force generator 24 is connected to only the controller 50. Accordingly, the piston drive force generator 24 uses the power supplied to the controller 50 to produce a drive force for driving the piston 45.

The power path when the piston return switch 70 has been operated is as shown in FIG. 9B. In this case, since the piston return switch 70 has been operated, the piston return switch 70 is in the closed state shown in FIG. 9B. At this point the terminals A and B are connected within the power path controller 75. Thus, the power supply 40 is connected not only to the controller 50, but also to the piston drive force generator 24.

That is, the piston drive force generator 24 is connected directly to the power supply 40. Accordingly, the piston drive force generator 24 can produce drive force for driving the piston 45 by receiving power directly from the power supply 40, without relying on power from the controller 50. More specifically, the piston drive force generator 24 (motor) rotates upon receiving power directly from the power supply 40. The rotation direction at this point is the direction in which the piston 45 is pulled out of the pharmaceutical cartridge 9 (upward). The polarity of the wiring when the power supply 40 and the piston drive force generator 24 are directly connected is the direction in which the piston 45 is pulled out of the pharmaceutical cartridge 9.

How the piston return switch 70 is used will now be described in specific terms.

Let us assume that the piston 45 cannot be taken out of the pharmaceutical cartridge 9 based on the operation of the controller 50, and the piston 45 is still inserted into the interior of the pharmaceutical cartridge 9. The user holds down the piston return switch 70 long enough for the piston 45 to be pulled out of the pharmaceutical cartridge 9. After this the user manually operates the protrusion 35a (see the first embodiment), puts the cartridge holder 11 in its open state, and takes out the pharmaceutical cartridge 9.

Alternatively, the user holds down the piston return switch 70 long enough for the piston 45 to be pulled out of the pharmaceutical cartridge 9. After this, instead of operating the protrusion 35a, the driver 31 is actuated. As shown in FIG. 9B, here, when the piston return switch 70 has been operated, the power supply 40 supplies power to both the piston drive force generator 24 and the controller 50. As shown in FIG. 8, the driver 31 is able to operate under the control of the driver control circuit 54 and the CPU 52 of the controller 50 to which power is supplied. Upward operation of the driver 31 automatically unlatches the holder latching component 11c from the latching receiver 33. Consequently, the user puts the cartridge holder 11 in its open state and takes out the pharmaceutical cartridge 9.

As discussed above, if control by the controller 50 becomes impossible, the piston drive force generator 24 can no longer produce drive force for the piston 45 on the basis of control by the controller 50. In a state in which the piston 45 has been inserted into the pharmaceutical cartridge 9, the piston 45 becomes an obstacle, and the pharmaceutical cartridge 9 cannot be taken out.

In this situation, as discussed above, the user operates the piston return switch 70. Consequently, the piston drive force generator 24 receives power directly from the power supply 40 and can produce drive force for the piston 45. That is, even if control by the controller 50 should become impossible, the piston drive force generator 24 can still produce drive force for the piston 45. Therefore, the piston 45 inserted into the pharmaceutical cartridge 9 can be pulled out of the pharmaceutical cartridge 9. Also, once the piston 45 is pulled out of the pharmaceutical cartridge 9, the pharmaceutical cartridge 9 can be taken out of the cartridge holder 11 without any trouble.

Also, in the above embodiment, power is supplied from the power supply 40 to the controller 50 even when the piston return switch 70 has been operated. Even if the controller 50 cannot control the piston drive force generator 24, there will be situations in which it can control another driver. Thus, even if the piston return switch 70 has been operated, power can be supplied directly from the power supply 40 to the piston drive force generator 24 to drive the piston 45, while power can be supplied to the controller 50 to actuate a driver that the controller 50 can control. Furthermore, once the inoperable controller 50 becomes operable again, the piston drive force generator 24 will be able to produce drive force for the piston 45 based on the power from the controller 50.

Also, whether power is supplied directly from the power supply 40 to the piston drive force generator 24, or power is supplied from the power supply 40 through the controller 50 to the piston drive force generator 24 is determined by whether or not the piston return switch 70 is operated. That is, the operation of the piston return switch 70 is linked to the production of a power path that electrically connects the power supply 40 directly to the piston drive force generator 24. Thus, how the power is supplied to the piston drive force generator 24 is obvious to the user, making the device easier to operate. To put this another way, the piston return switch 70 handles commands for whether or not to supply power from the power supply 40 directly. If a command received by the piston return switch 70 is transmitted, the power path controller 75 creates a power path as discussed above on the basis of this command.

The piston return switch 70 is provided inside the hole 71 in the outer wall of the main body case 1a. Accordingly, this prevents the piston return switch 70 from being accidentally operated by contact with the user's hand, another member, or the like.

(2) Second Method

Figure 10A:
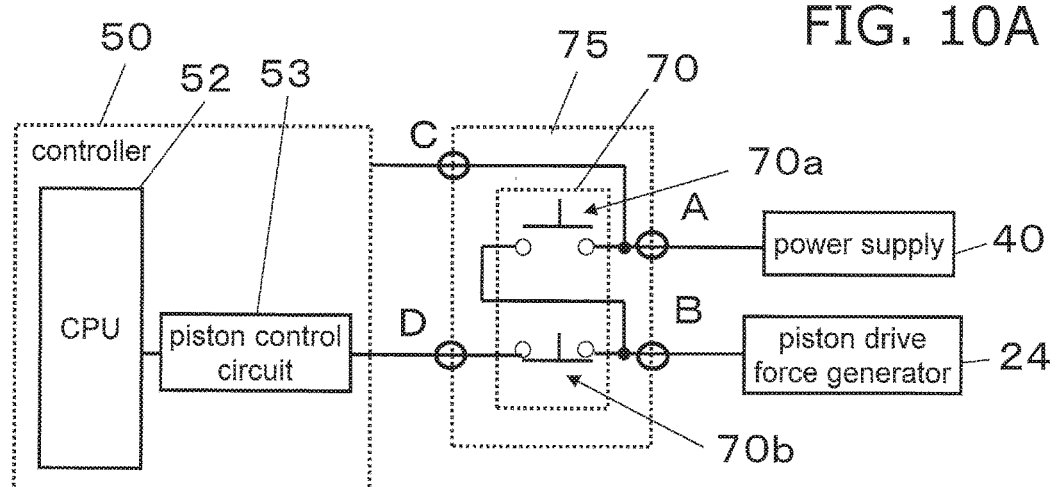
FIG. 10A shows the power path when a piston return switch has not been pressed in a second method.
Figure 10B:
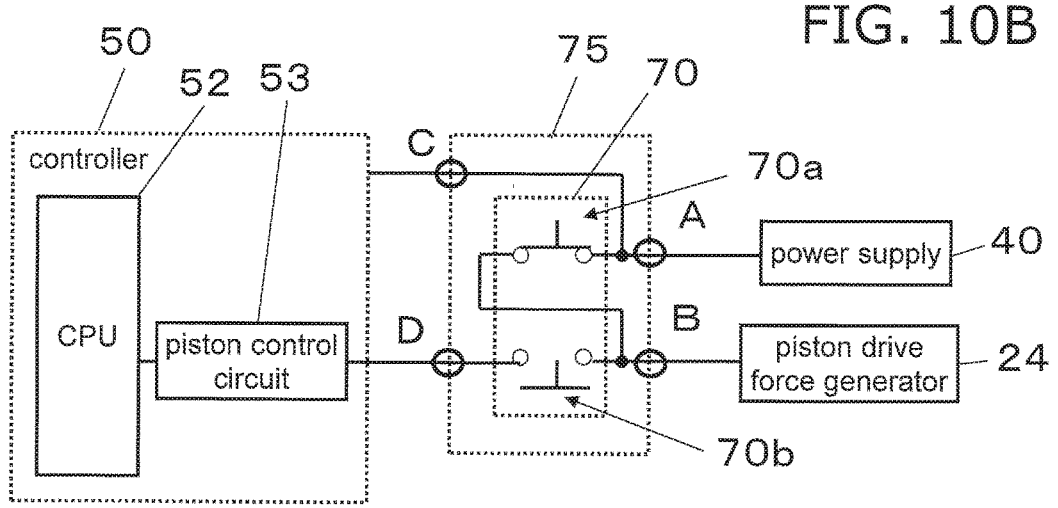
FIG. 10B shows the power path when the piston return switch has been pressed in the second method.

In the second method, the external view and control block diagram of the pharmaceutical injection device 200 are the same as FIGS. 7 and 8 in the case of the first method. The second method differs from the first method in the power path when the piston return switch 70 is and is not operated. FIG. 10A shows the power path in the second method when the piston return switch 70 has not been pressed. FIG. 10B shows the power path in the second method when the piston return switch 70 has been pressed.

The power path controller 75 has four terminals A, B, C, and D, for example. The terminal A is connected to the power supply 40. The terminal B is connected to the piston drive force generator 24. The terminal C is connected to the controller 50. The terminal D is connected to the piston control circuit 53. Inside the power path controller 75, the terminals A and C are linked, regardless of whether or not the piston return switch 70 is operated.

The piston return switch 70 has a first switch 70a and a second switch 70b. The power path when the piston return switch 70 has not been operated is as shown in FIG. 10A. In this case, since the piston return switch 70 has not been operated, the first switch 70a is open and the second switch 70b is closed, as shown in FIG. 10A. At this point the terminals A and B are not connected. Thus, the power supply 40 is connected to only the controller 50, and the piston drive force generator 24 is connected to only the controller 50. Accordingly, the piston drive force generator 24 uses the power supplied to the controller 50 to produce drive force for driving the piston 45.

The power path when the piston return switch 70 has been operated is as shown in FIG. 10B. In this case, since the piston return switch 70 has been operated, the first switch 70a is closed and the second switch 70b is open, as shown in FIG. 10B. At this point the terminals A and B are connected inside the power path controller 75. The terminals B and D, however, are not connected.

In FIG. 10B, the power supply 40 is connected not only to the controller 50, but also to the piston drive force generator 24. Thus, the piston drive force generator 24 is connected directly to the power supply 40. Accordingly, the piston drive force generator 24 can produce drive force for driving the piston 45 on the basis of the power from the power supply 40, without relying on the power from the controller 50.

Thus, the same effect can be obtained as in the first method.

That is, when the piston return switch 70 is operated, the piston drive force generator 24 receives the supply of power directly from the power supply 40. This allows drive force for the piston 45 to be produced. Thus, even if control by the controller 50 should become impossible, the piston drive force generator 24 will still be able to produce the drive force for the piston 45. The piston 45 that is inserted into the pharmaceutical cartridge 9 can then be pulled out of the pharmaceutical cartridge 9. Also, even if the piston return switch 70 has been operated, power will be supplied from the power supply 40 to the controller 50. Even if the controller 50 is unable to control the piston drive force generator 24, it may still be able to control another driver. Thus, even if the piston return switch 70 has been operated, power will be supplied directly from the power supply 40 to the piston drive force generator 24 to drive the piston 45, while power will be supplied to the controller 50 to allow the controller 50 to actuate a driver that it can control. The polarity of the wiring and the rotation direction of the piston drive force generator 24 (motor) at this point are the same as in the first method. In FIG. 10B, since the terminals B and D are not connected, the controller 50 and the piston drive force generator 24 are not connected. Thus, even if the controller 50 should malfunction, the piston drive force generator 24 will not be affected by erroneous control from the controller 50.

The operation of the piston return switch 70 by the user and so forth are the same as in the first method.

With the first and second methods in the above embodiment, the user holds down the piston return switch 70 long enough for the piston 45 to be pulled out of the pharmaceutical cartridge 9. However, a detector (not shown) may detect that the piston 45 has been pulled out of the pharmaceutical cartridge 9. The user can then stop the operation of the piston return switch 70 on the basis of this detection result.

Third Embodiment

In the third embodiment, we will describe a configuration and method for taking the pharmaceutical cartridge 9 out of the cartridge holder 11 when a problem has occurred in the driver 31 of the cartridge holder 11, the controller 50, the power supply 40, etc.

The basic configuration of the pharmaceutical injection device 100 is the same as that shown in FIGS. 1 to 6 and described in the first embodiment. We will therefore describe only the components that are different from the first embodiment, and description of those components that are the same as in the first embodiment will be either omitted or simplified as needed.

As shown in FIGS. 3A, 3B, etc., the cartridge holder mechanism 10 includes the cartridge holder 11, the injection needle mounting component 13, the fulcrum 15, and the removal spring 17. The takeout mechanism 30 includes the driver 31, the latching receiver main body 32, the latching receiver 33, the drive spring 34, and the manipulation component 35. The cartridge holder 11 and injection needle mounting component 13 pertaining to the third embodiment will now be described.

(1) Cartridge Holder 11

Figure 11:
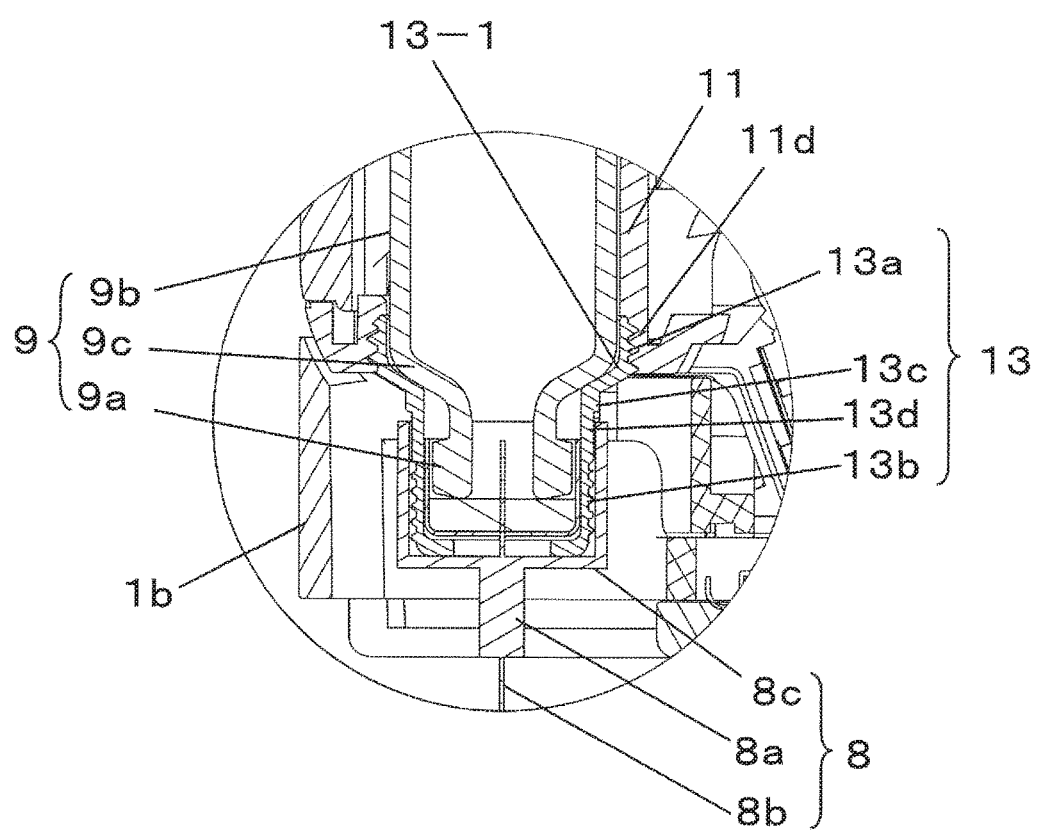
FIG. 11 is a detail front cross section of the connection between the cartridge holder and the injection needle mounting component.
Figure 12:
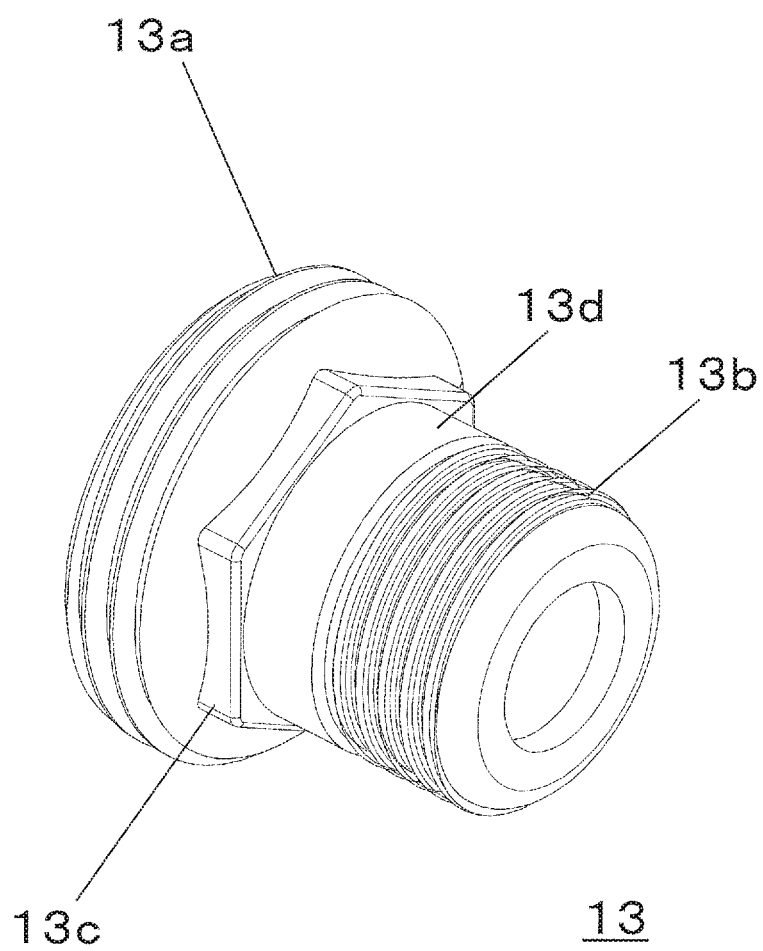
FIG. 12 is an external oblique view of the injection needle mounting component.

FIG. 11 is a detail front cross section of the connected portions of the cartridge holder 11 and the injection needle mounting component 13. FIG. 12 is an oblique view of the injection needle mounting component 13. As shown in FIGS. 1 and 2, the cartridge holder 11 is a member that can be housed in the interior of the main body case 1a, and is provided openably and closeably with respect to the main body case 1a.

As shown in FIGS. 1 to 4 and FIG. 11, the cartridge holder 11 has the outer wall 11a, the holding space 11b, the holder latching component 11c, and a holder-side connector 11d.

The outer wall 11a is flush with the outer surface of the main body case 1a when the cartridge holder 11 is closed and housed inside the main body case 1a.

The holding space 11b of the cartridge holder 11 is a space that holds the cylindrical pharmaceutical cartridge 9, for example. A pharmaceutical that is to be administered by the pharmaceutical injection device 100 is sealed inside the pharmaceutical cartridge 9.

The holder latching component 11c latches to the latching receiver 33 of the takeout mechanism 30. The cartridge holder 11 is housed inside the main body case 1a when the cartridge holder 11 is closed and the holder latching component 11c latches to the latching receiver 33. The cartridge holder 11 housed in the main body case 1a here is subjected to a biasing force in the opening direction by the removal spring 17. Thus, the holder latching component 11c keeps the cartridge holder 11 closed with respect to the main body case 1a against the biasing force of the removal spring 17. The holder latching component 11c is formed so as to stick out toward the latching receiver 33 side, so as to allow latching to the latching receiver 33.

The holder-side connector 11d is the portion to which a first connector 13a of the injection needle mounting component 13 is connected. The holder-side connector 11d is provided to the end of the cartridge holder 11. Connecting the holder-side connector 11d and the first connector 13a fixes the injection needle mounting component 13 to the cartridge holder 11. The holder-side connector 11d is formed on the inside wall of the cartridge holder 11. The holder-side connector 11d is formed on the inside wall of the cartridge holder 11 by insert-molding an injection needle mounting component 13 made of metal, for example, to a cartridge holder 11 made of a resin material, for example.

(2) Injection Needle Mounting Component 13

As shown in FIGS. 3A to 4, FIG. 11, FIG. 12, etc., the injection needle mounting component 13 is a substantially cylindrical member, and is used to connect the injection needle component 8 to the cartridge holder 11. The injection needle mounting component 13 is provided to the lower portion, that is, the end, of the cartridge holder 11. The pharmaceutical cartridge 9 is inserted from above the injection needle mounting component 13, and the tip 9a and shoulder 9c of the pharmaceutical cartridge 9 (FIG. 11) are located inside the injection needle mounting component 13. Meanwhile, the injection needle component 8 is inserted from below the injection needle mounting component 13. Here, the injection needle component 8 includes the injection needle base 8a (the base of the needle 8b), the hollow needle 8b, and the attachment member 8c. The attachment member 8c is used to connect the injection needle mounting component 13 and the injection needle component 8. When the attachment member 8c is attached to the injection needle mounting component 13, the needle 8b passes into the interior of the pharmaceutical cartridge 9, allowing the pharmaceutical in the pharmaceutical cartridge 9 to be administered.

The injection needle mounting component 13 has the first connector 13a, a second connector 13b, a convex part 13c, and a main body part 13d. The first connector 13a, the main body part 13d, and the second connector 13b are linked in that order along the insertion direction of the needle 8b. The convex part 13c is formed adjacent to the first connector 13a and so as to stick out from the outer face of the main body part 13d.

As shown in FIG. 11, a through-hole 13-1 is formed in the center part of the cylindrical injection needle mounting component 13. The through-hole 13-1 is such that the inside diameter at the first connector 13a is different from the inside diameter at the main body part 13d. More specifically, the inside diameter at the first connector 13a is greater than the inside diameter at the main body part 13d. At the linked portion between the first connector 13a and the main body part 13d, the inside diameter gradually narrows from the first connector 13a toward the main body part 13d.

As shown in FIG. 11, the pharmaceutical cartridge 9 has the tip 9a, the pharmaceutical cartridge main body 9b, and the shoulder 9c. The tip 9a is the distal end portion of the pharmaceutical cartridge 9, and is the portion where the distal end of the needle 8b is inserted. The pharmaceutical cartridge main body 9b is the portion that mainly holds the pharmaceutical. The shoulder 9c is provided between the tip 9a and the pharmaceutical cartridge main body 9b. The outside diameter of the tip 9a is less than the outside diameter of the pharmaceutical cartridge main body 9b, and the outside diameter at the shoulder 9c narrows from the pharmaceutical cartridge main body 9b toward the tip 9a.

Thus, as shown in FIG. 11, the shoulder 9c of the pharmaceutical cartridge 9 is supported at the linked portion between the first connector 13a and the main body part 13d where the inside diameter narrows.

The configuration of the various components will now be described.

(2-1) Main Body Part 13d

The main body part 13d is provided between the first connector 13a and the second connector 13b. The outside diameter of the main body part 13d is about the same as that of the second connector 13b, for example.

As discussed above, the through-hole 13-1 is formed in the center part of the cylindrical injection needle mounting component 13. Thus, the main body part 13d is formed in a substantially cylindrical shape, and the tip 9a of the pharmaceutical cartridge 9 can pass through as shown in FIG. 11. Furthermore, as discussed above, since the inside diameter of the main body part 13d is less than the inside diameter of the first connector 13a, only the tip 9a of the pharmaceutical cartridge 9 passes through to the main body part 13d.

(2-2) First connector 13a

As shown in FIG. 12, the first connector 13a is formed linked to the main body part 13d on the opposite side from the second connector 13b. Also, the convex part 13c is formed on the first connector 13a, on the second connector 13b side.

The first connector 13a is connected to the holder-side connector 11d of the cartridge holder 11. As shown in FIG. 11, for example, the first connector 13a and the holder-side connector 11d are mated together in a state in which the outer face of the first connector 13a is touching the inner face of the holder-side connector 11d. This fixes the injection needle mounting component 13 to the cartridge holder 11.

The outside diameter of the first connector 13a is greater than the outside diameter of the convex part 13c, the main body part 13d, and the second connector 13b.

The through-hole 13-1 is formed in the center part of the cylindrical injection needle mounting component 13. Thus, the first connector 13a is formed in a substantially cylindrical shape, and the tip 9a and the end of the pharmaceutical cartridge main body 9b can pass through as shown in FIG. 11. Since the inside diameter of the first connector 13a is greater than the inside diameter of the main body part 13d as mentioned above, not just the tip 9a, but also the end of the pharmaceutical cartridge main body 9b also passes through.

The first connector 13a is formed with male or female threads, for example. If the first connector 13a has male threads, then the holder-side connector 11d has female threads. On the other hand, if the first connector 13a has female threads, then the holder-side connector 11d has male threads.

(2-3) Second Connector 13b

As shown in FIG. 12, the second connector 13b is formed linked to the main body part 13d, on the opposite side from the first connector 13a.

The injection needle component 8 is connected to the second connector 13b. More specifically, as shown in FIG. 11, the cylindrical attachment member 8c is fitted to the outside of the second connector 13b so as to cover the second connector 13b.

For example, as shown in FIG. 11, the second connector 13b is formed with threads, the attachment member 8c is formed in a cylindrical shape, and these are connected to each other by bringing the second connector 13b into contact with the inner walls of the attachment member 8c. Alternatively, both the second connector 13b and the attachment member 8c are formed with threads, and are connected by mating them together. Consequently, the injection needle component 8 having the needle 8b, etc., is attached to the lower portion of the injection needle mounting component 13, that is, on the second connector 13b side.

The second connector 13b is formed in a substantially cylindrical shape. Thus, as shown in FIG. 11, the tip 9a of the pharmaceutical cartridge 9 can pass through at least part of the second connector 13b.

(2-4) Convex Part 13c

The convex part 13c is provided so as to stick out from the outer face of the main body part 13d. In other words, the convex part 13c is formed so as to stick out with respect to the main body part 13d, toward the outside in the radial direction of the main body part 13d.

Also, the convex part 13c is formed so as to be adjacent to the first connector 13a at the main body part 13d. That is, the convex part 13c is formed more on the first connector 13a side than the second connector 13b side out of the main body part 13d. In FIG. 12, the convex part 13c and the first connector 13a are formed linked together, but the convex part 13c and the first connector 13a may instead be separate as long as they work in conjunction.

The convex part 13c is the portion that is subjected to pressure when the first connector 13a and the holder-side connector 11d are disconnected. Pressure can be applied to the convex part 13c by pulling, rotating, or the like with a tool, a hand, etc.

The holder-side connector 11d here is provided to the end of the cartridge holder 11. When the first connector 13a is connected to the holder-side connector 11d, the convex part 13c sticks out at the end of the cartridge holder 11. Thus, the user can easily pull, turn, or otherwise operate the convex part 13c sticking out from the end of the cartridge holder 11 with a tool, a hand, etc.

Also, the convex part 13c is formed in a substantially cylindrical shape, and the tip 9a of the pharmaceutical cartridge 9 is able to pass through as shown in FIG. 11. Since the inside diameter of the main body part 13d (also the inside diameter of the convex part 13c) is less than the inside diameter of the first connector 13a as mentioned above, only the tip 9a of the pharmaceutical cartridge 9 passes through to the convex part 13c.

Furthermore, the outside diameter of the convex part 13c is smaller than the outside diameter of the first connector 13a, and is also greater than the outside diameter of the second connector 13b and the main body part 13d.

As shown in FIG. 12, the convex part 13c is formed such that its shape is substantially that of a regular hexagon as viewed in the direction in which the needle 8b of the injection needle component 8 is inserted. However, the shape of the convex part 13c is not limited to that of a regular hexagon. The convex part 13c may be, for example, in the form of a digon, a triangle, a quadrangle, a pentagon, a hexagon, or another polygon with more sides. For instance, the convex part 13c can be easily pulled, turned, or otherwise operated by gripping two opposing sides of a regular hexagon or a polygon with a tool, a hand, or the like.

The convex part 13c may also be formed so that a protrusion on one side sticks out from the main body part 13d. However, a polygonal shape having two substantially parallel opposing sides is preferable in that this allows it to be easily gripped or manipulated with a tool, a hand, etc.

Examples of the tool here include an open-end wrench, a box wrench, and other such tightening tools. For example, the convex part 13c is formed as a regular hexagon that mates with an existing hex wrench, so that it can be easily manipulated with a commercially available wrench. The term "open-end wrench" here refers to a tool that is open at its distal end, and is used to tighten or loosen by gripping two ends of the convex part 13c. A "box wrench" is a tool that is substantially ring-shaped, and is used to tighten or loosen by mating with the convex part 13c.

Here, the above-mentioned first connector 13a, second connector 13b, convex part 13c, and main body part 13d may be formed integrally in the injection needle mounting component 13. This will help suppress the looseness that can occur when the injection needle component 8 is attached to the injection needle mounting component 13. Also, it is easier to manufacture the injection needle mounting component 13 this way than when the first connector 13a, the second connector 13b, the convex part 13c, and the main body part 13d are all separate pieces.

(3) Procedure for Removing Pharmaceutical Cartridge 9

The user usually operates a certain button or the like when the pharmaceutical cartridge 9 is to be replaced. Consequently, the drive of the driver 31 puts the cartridge holder 11 in an open state. The user takes the used pharmaceutical cartridge 9 out of the open cartridge holder 11, and puts a fresh pharmaceutical cartridge 9 into the cartridge holder 11.

There may be situations in which the driver 31 that opens the cartridge holder 11 malfunctions, or the controller 50 of the driver 31 or the power supply 40 that supplies power to the driver 31 malfunctions. If this happens, the cartridge holder 11 cannot be opened by the driver 31 as discussed above, and the pharmaceutical cartridge 9 cannot be taken out. The user then applies pressure to the convex part 13c by pulling, turning, or otherwise manipulating it with a tool, a hand, or the like, and pulls the injection needle mounting component 13 away from the cartridge holder 11. The user then uses a tool, a hand, or the like to take the pharmaceutical cartridge 9 out of the cartridge holder 11 from which the injection needle mounting component 13 has been removed. That is, the pharmaceutical cartridge 9 can be taken out of the cartridge holder 11 even if a problem occurs in the power supply 40, the controller 50, the driver 31 or the cartridge holder 11, or the like.

The procedure will now be described in specific terms.

Figure 13A:
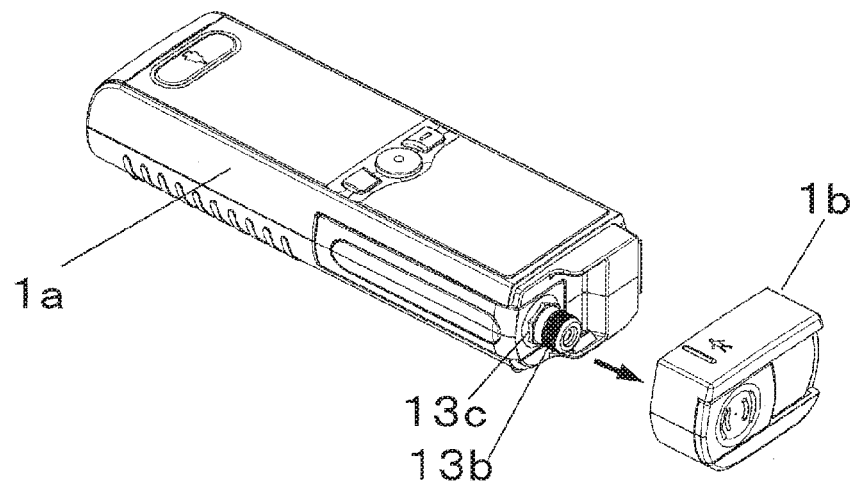
FIG. 13A is a diagram (1) of an example of the step of removing the injection needle mounting component from the main body case.
Figure 13B:
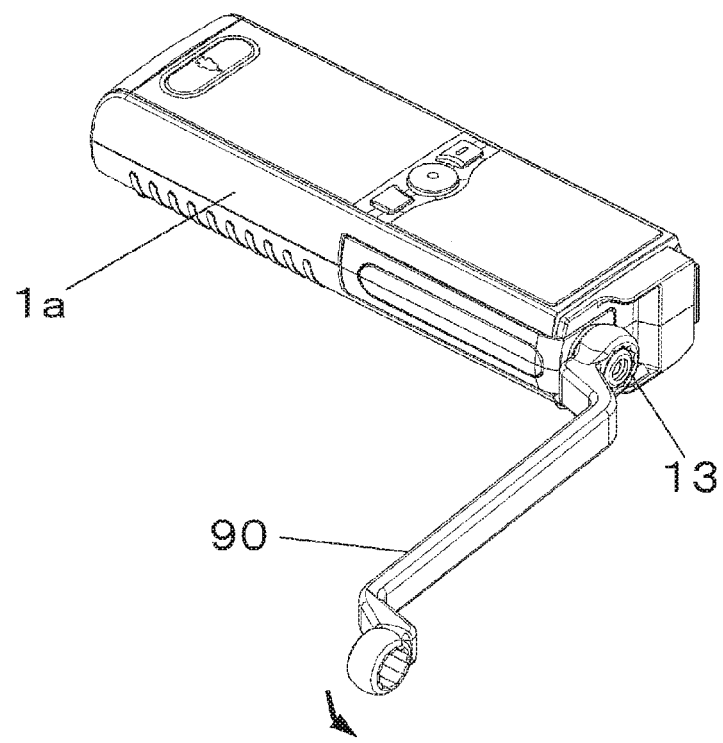
FIG. 13B is a diagram (2) of an example of the step of removing the injection needle mounting component from the main body case.
Figure 13C:
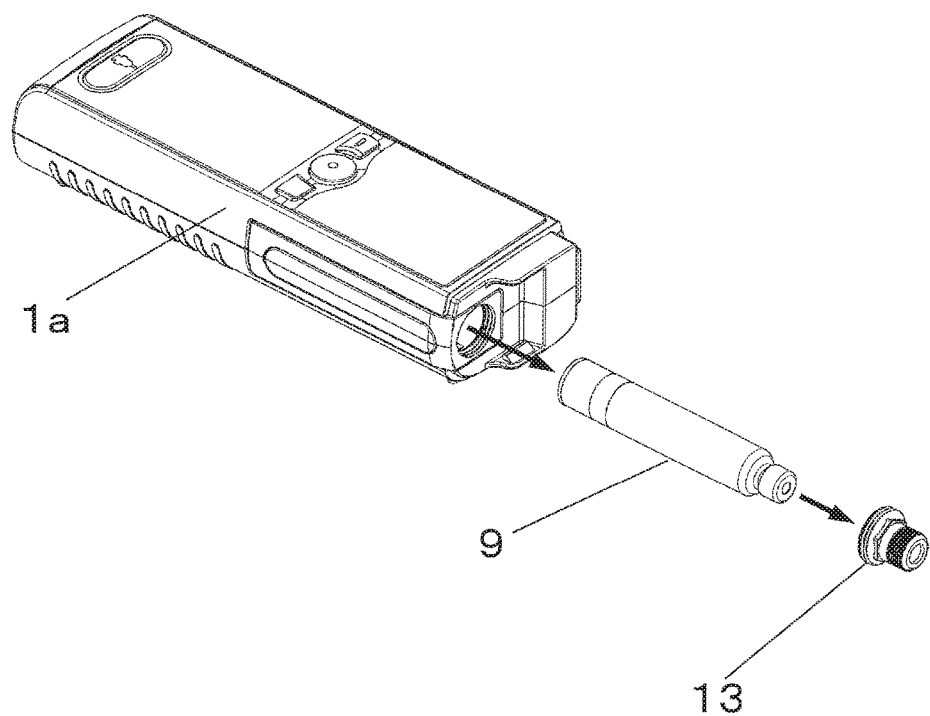
FIG. 13C is a diagram (3) of an example of the step of removing the injection needle mounting component from the main body case.

FIGS. 13A to 13C show an example of the sequence of steps for removing the injection needle mounting component 13 from the main body case 1a.

First, as shown in FIG. 13A, the user removes the cap 1b from the main body case 1a. The injection needle mounting component 13 is fixed to the cartridge holder 11 by connecting the first connector 13a of the injection needle mounting component 13 to the holder-side connector 11d of the cartridge holder 11. Since the first connector 13a is connected inside the cartridge holder 11 at this point, the convex part 13c and the second connector 13b stick out from the end of the cartridge holder 11.

Next, as shown in FIG. 13B, the user uses a box wrench 90, for example, on the convex part 13c of the injection needle mounting component 13 to turn it in the direction of loosening the first connector 13a and the holder-side connector 11d. The box wrench 90 here is used on the convex part 13c, but as discussed above, the tool is not limited to the box wrench 90. For example, the user may turn the convex part 13c by hand.

When the convex part 13c is turned with the box wrench 90, the first connector 13a and the holder-side connector 11d are disconnected, and the injection needle mounting component 13 turns. As shown in FIG. 13C, this causes the injection needle mounting component 13 to be removed from the main body case 1a.

As shown in FIG. 11, the tip 9a of the pharmaceutical cartridge 9 sticks out from the cartridge holder 11. Thus, when the injection needle mounting component 13 has been removed from the cartridge holder 11, the tip 9a of the pharmaceutical cartridge 9 is exposed from the end of the cartridge holder 11. In this case, the user can use a tool, a hand, or the like to grip the exposed tip 9a of the pharmaceutical cartridge 9 and remove it from the cartridge holder 11.

Meanwhile, when the injection needle mounting component 13 has been removed from the cartridge holder 11, there are times when the pharmaceutical cartridge 9 is housed inside the cartridge holder 11. In this case, the user can insert a slender tool into the cartridge holder 11, grip the tip 9a of the pharmaceutical cartridge 9, and take the pharmaceutical cartridge 9 out of the cartridge holder 11.

As discussed above, the through-hole 13-1, through which the tip 9a of the pharmaceutical cartridge 9 can pass as shown in FIG. 11, is provided to the center part of the injection needle mounting component 13. After the injection needle mounting component 13 has been mounted to the distal end of the cartridge holder 11, the pharmaceutical cartridge 9 is pushed out under the cartridge holder 11, that is, toward the distal end. Consequently, the tip 9a of the pharmaceutical cartridge 9 goes through the through-hole 13-1 of the injection needle mounting component 13.

At this point, when the injection needle mounting component 13 is removed from the cartridge holder 11, the pharmaceutical cartridge 9 sticks out of the cartridge holder 11 by the amount it has passed through the through-hole 13-1. Thus, the user can take the pharmaceutical cartridge 9 out of the cartridge holder 11 by gripping the protruding tip 9a of the pharmaceutical cartridge 9 with a tool, a hand, or the like.

Also, as discussed above, the convex part 13c is formed more on the first connector 13a side connected to the cartridge holder 11, than on the second connector 13b side. That is, the convex part 13c is provided to the portion that is closer to the connected portion of the cartridge holder 11 and the injection needle mounting component 13 than the second connector 13b. Accordingly, when pressure is applied to the convex part 13c, the force for disconnecting the cartridge holder 11 from the injection needle mounting component 13 is readily transmitted to the connected portion via the convex part 13c. Consequently, the user can easily pull the injection needle mounting component 13 away from the cartridge holder 11 by applying pressure to the convex part 13c.

Also, as discussed above, since the outside diameter of the convex part 13c is less than the outside diameter of the first connector 13a, the convex part 13c tends not to get in the way when the injection needle mounting component 13 is connected to the cartridge holder 11. Also, the outside diameter of the convex part 13c is greater than the outside diameter of the second connector 13b. Thus, the second connector 13b does not pose an obstacle to pulling the injection needle mounting component 13 away from the cartridge holder 11, and the user can easily manipulate the convex part 13c with a tool, a hand, or the like from the second connector 13b side.

(4) Modification Example (4-1)

In the third embodiment above, the manipulation component 35 having the protrusion 35a and the protrusion placement part 35b is provided. Furthermore, the convex part 13c is provided to the injection needle mounting component 13 in the above embodiment. However, the manipulation component 35 does not necessarily have to be provided.

That is, just the injection needle mounting component 13 having the convex part 13c may be provided to the pharmaceutical injection device 100 for situations in which a problem occurs in the driver 31, etc., and the cartridge holder 11 cannot be opened. Consequently, at least the convex part 13c can be operated to remove the injection needle mounting component 13 from the cartridge holder 11, and the pharmaceutical cartridge 9 can be taken out of the cartridge holder 11.

However, when the manipulation component 35 is provided in addition to the convex part 13c, the user can selectively perform the operation for removing the pharmaceutical cartridge 9.

That is, in the first case, the user may operate the manipulation component 35 to open the cartridge holder 11, and take the pharmaceutical cartridge 9 out of the cartridge holder 11. In the second case, the user may remove the injection needle mounting component 13 from the cartridge holder 11, and take the pharmaceutical cartridge 9 out of the cartridge holder 11.

For example, there are situations in which the cartridge holder 11 cannot be opened because the pharmaceutical cartridge 9 has been inserted into the cartridge holder 11. In this case, the user removes the injection needle mounting component 13 and takes the pharmaceutical cartridge 9 out of the cartridge holder 11. On the other hand, there are situations in which no pharmaceutical cartridge 9 has been inserted in the cartridge holder 11, and the cartridge holder 11 can be opened. In this case, the user operates the manipulation component 35 to open the cartridge holder 11, and takes the pharmaceutical cartridge 9 out of the cartridge holder 11.

(4-2)

In the third embodiment above, the through-hole 13-1, through which the pharmaceutical cartridge 9 can pass as shown in FIG. 11, is provided to the center part of the injection needle mounting component 13. However, the through-hole 13-1 of the injection needle mounting component 13 should at least be large enough to allow the needle 8b of the injection needle component 8 to pass through. In this case, the tip 9a of the pharmaceutical cartridge 9 does not stick out from the end of the cartridge holder 11. That is, even if the injection needle mounting component 13 is removed from the cartridge holder 11, the tip 9a of the pharmaceutical cartridge 9 will still not be exposed from the end of the cartridge holder 11. In this case, the user grips the tip 9a of the pharmaceutical cartridge 9 located inside the cartridge holder 11 with a tool or the like, and takes it out of the cartridge holder 11.

INDUSTRIAL APPLICABILITY

Certain implementations can be utilized in a wide variety of pharmaceutical injection devices since it allows a pharmaceutical cartridge to be taken out of the pharmaceutical injection device even if the pharmaceutical injection device cannot be automatically driven by electric drive.

The invention claimed is:

1. A pharmaceutical injection device, comprising:
a main body case;
a cartridge holder that has a holding space that is provided in an interior of the main body case so that the cartridge holder is openable and closeable with respect to a side face of the main body case, the cartridge holder being capable of holding a pharmaceutical cartridge, and the cartridge holder having a holder latching component for maintaining a closed state;
a latching receiver configured to latch or release the holder latching component according to whether the cartridge holder is closed or open;
a driver configured to automatically release a latching of the latching receiver and the holder latching component by driving the latching receiver upon receiving power; and
a manipulation component for manually releasing the latching of the latching receiver and the holder latching component by moving the latching receiver upon being subjected to external pressure,
wherein:
a part of the manipulation component consists of a protrusion that sticks out further than a remainder of the manipulation component;
the latching receiver is configured to be manually moved by application of the external pressure to the protrusion so as to release the latching between the latching receiver and the holder latching component;
the protrusion is provided to an opening inside the main body case;
a power supply holding space for holding a removable power supply is provided in the interior of the main body case; and
the opening inside the main body case is provided to the power supply holding space.

2. The pharmaceutical injection device according to claim 1,
wherein the holder latching component and the latching receiver are defined along a direction in which the manipulation component is configured to move the latching receiver with the external pressure.

3. The pharmaceutical injection device according to claim 1,
wherein the opening inside the main body case defines a movable range when the protrusion is subjected to the external pressure.

4. A pharmaceutical injection device comprising:
a main body case;
a cartridge holder that has a holding space that is provided in an interior of the main body case so that the cartridge holder is openable and closeable with respect to a side face of the main body case, the cartridge holder being capable of holding a pharmaceutical cartridge, and the cartridge holder having a holder latching component for maintaining a closed state;
a latching receiver configured to latch or release the holder latching component according to whether the cartridge holder is closed or open;
a driver configured to automatically release a latching of the latching receiver and the holder latching component by driving the latching receiver upon receiving power; and
a manipulation component for manually releasing the latching of the latching receiver and the holder latching component by moving the latching receiver upon being subjected to external pressure;
a power supply;
a piston configured to be inserted into or pulled out of the pharmaceutical cartridge;
a piston drive force generator configured to generate drive force supplied to the piston;
a controller configured to control the piston drive force generator upon receiving power from the power supply;
a power path controller configured to allow the power from the power supply to be supplied directly to the piston drive force generator; and
a switch configured to receive a command for whether or not to supply the power from the power supply directly to the piston drive force generator, and transfer the command to the power path controller.

5. The pharmaceutical injection device according to claim 4,
wherein, when the switch is not operated, the power path controller connects the piston drive force generator to the power supply via the controller, and provides power from the power supply to the piston drive force generator via the controller, and when the switch is operated, the power path controller connects the piston drive force generator to the power supply via the controller, while connecting the piston drive force generator directly to the power supply to provide the power from the power supply directly to the piston drive force generator.

6. The pharmaceutical injection device according to claim 4, wherein, when the switch is not operated, the power path controller connects the piston drive force generator to the power supply via the controller, and provides power from the power supply to the piston drive force generator via the controller, and when the switch is operated, the power path controller connects the power supply and the controller, disconnects the controller from the piston drive force generator, and connects the piston drive force generator directly to the power supply to provide the power from the power supply directly to the piston drive force generator.

7. The pharmaceutical injection device according to claim 4, wherein, only when the switch is operated, the power path controller provides the power from the power supply directly to the piston drive force generator.

8. The pharmaceutical injection device according to claim 4, wherein the switch is provided in a hole in an outer wall of the main body case.

* * * * *